US012805736B1

(12) United States Patent
Torstrick et al.

(10) Patent No.: US 12,805,736 B1
(45) **Date of Patent: *Nov. 24, 2026**

(54) PHOTOPLETHYSMOGRAPHY SENSORS AND PROCESSES

(71) Applicant: Huxley Medical, Inc., Atlanta, GA (US)

(72) Inventors: Brennan Torstrick, Atlanta, GA (US); Mohsen Safaei Mohammadabadi, Smyrna, GA (US)

(73) Assignee: Huxley Medical, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/945,072

(22) Filed: Nov. 12, 2024

Related U.S. Application Data

(63) Continuation of application No. 17/821,990, filed on Aug. 24, 2022, now Pat. No. 12,279,853.

(60) Provisional application No. 63/236,511, filed on Aug. 24, 2021.

(51) Int. Cl.

| | |
|---|---|
| ***A61B 5/1455*** | (2006.01) |
| ***A61B 5/00*** | (2006.01) |
| ***A61B 5/024*** | (2006.01) |
| ***A61B 5/282*** | (2021.01) |

(52) U.S. Cl.
CPC .......... *A61B 5/02416* (2013.01); *A61B 5/282* (2021.01); *A61B 5/6833* (2013.01); *A61B 2562/164* (2013.01); *A61B 2562/166* (2013.01)

(58) Field of Classification Search
CPC .................................................... A61B 5/1455
See application file for complete search history.

(56) References Cited

U.S. PATENT DOCUMENTS

| | | | |
|---|---|---|---|
| 112,102 | A | 2/1871 | Whittemore |
| 142,988 | A | 9/1873 | Bbobstotf |
| 162,627 | A | 4/1875 | Coyle |
| 210,034 | A | 11/1878 | Higgins et al. |

(Continued)

FOREIGN PATENT DOCUMENTS

| | | | |
|---|---|---|---|
| AU | 2015253309 B2 | 2/2021 | |
| CN | 218978894 U | 5/2023 | |

(Continued)

OTHER PUBLICATIONS

Shafiq, et al., Data Descriptor: Multimodal chest surface motion data for respiratory and cardiovascular monitoring applications, Scientific Data, Apr. 2017, 12 pages.

(Continued)

*Primary Examiner* — Marjan Fardanesh
(74) *Attorney, Agent, or Firm* — Husch Blackwell LLP; Bryan D. Stewart

(57) ABSTRACT

The present disclosure relates to devices and processes that produce superior photoplethysmography (PPG) signals. In various embodiments, the present devices and processes leverage load backing, conformal contact, and strain isolation mechanisms to produce higher quality and amplitude PPG signals, and provide more repeatable results than previous devices and processes. In at least one embodiment, the devices discussed herein include a rigid support structure and elastic spacer for supporting a PPG sensor and various adhesive layers.

14 Claims, 15 Drawing Sheets

(56) References Cited

U.S. PATENT DOCUMENTS

| | | | |
|---|---|---|---|
| 213,007 | A | 3/1879 | Thayee |
| 825,537 | A | 7/1906 | Macmillan |
| D47,333 | S | 5/1915 | Kleinschmidt |
| 1,248,586 | A | 12/1917 | Wood |
| D130,033 | S | 10/1941 | Reynolds |
| 3,052,232 | A | 9/1962 | Zworykin et al. |
| 3,195,535 | A | 7/1965 | Westermann |
| 3,638,642 | A | 2/1972 | Heflin, Sr. |
| 4,104,728 | A | 8/1978 | Kasubuchi |
| 4,121,573 | A | 10/1978 | Crovella et al. |
| D265,760 | S | 8/1982 | Lahay |
| D306,649 | S | 3/1990 | Lapicola et al. |
| 4,957,109 | A | 9/1990 | Groeger et al. |
| 5,016,202 | A | 5/1991 | Seibel et al. |
| 5,033,202 | A | 7/1991 | Chen |
| 5,050,613 | A | 9/1991 | Newman et al. |
| 5,251,286 | A | 10/1993 | Wiener et al. |
| 5,307,818 | A | 5/1994 | Segalowitz |
| D371,605 | S | 7/1996 | Wong et al. |
| 5,546,811 | A | 8/1996 | Rogers et al. |
| 5,633,711 | A | 5/1997 | Nelson et al. |
| 5,672,830 | A | 9/1997 | Rogers et al. |
| 5,734,470 | A | 3/1998 | Rogers et al. |
| 5,800,478 | A | 9/1998 | Chen et al. |
| 5,812,261 | A | 9/1998 | Nelson et al. |
| 5,951,881 | A | 9/1999 | Rogers et al. |
| 5,976,895 | A | 11/1999 | Cipkowski |
| 5,982,482 | A | 11/1999 | Nelson et al. |
| 6,016,202 | A | 1/2000 | Fuchs et al. |
| 6,033,202 | A | 3/2000 | Bao et al. |
| 6,052,185 | A | 4/2000 | Banet et al. |
| 6,069,703 | A | 5/2000 | Banet et al. |
| D434,494 | S | 11/2000 | Wilkinson et al. |
| 6,148,127 | A | 11/2000 | Adams et al. |
| 6,150,668 | A | 11/2000 | Bao et al. |
| 6,169,831 | B1 | 1/2001 | Adams et al. |
| 6,181,852 | B1 | 1/2001 | Adams et al. |
| 6,192,177 | B1 | 2/2001 | Amundson et al. |
| D442,693 | S | 5/2001 | Sternberg et al. |
| 6,252,253 | B1 | 6/2001 | Bao et al. |
| 6,256,100 | B1 | 7/2001 | Banet et al. |
| 6,275,629 | B1 | 8/2001 | Eggleton et al. |
| 6,285,812 | B1 | 9/2001 | Amundson et al. |
| 6,303,182 | B1 | 10/2001 | Eggleton et al. |
| 6,307,988 | B1 | 10/2001 | Eggleton et al. |
| 6,329,226 | B1 | 12/2001 | Jones et al. |
| 6,337,761 | B1 | 1/2002 | Rogers et al. |
| 6,351,585 | B1 | 2/2002 | Amundson et al. |
| 6,363,096 | B1 | 3/2002 | Dodabalapur et al. |
| 6,370,300 | B1 | 4/2002 | Eggleton et al. |
| 6,410,416 | B1 | 6/2002 | Dodabalapur et al. |
| 6,427,040 | B1 | 7/2002 | Ahuja et al. |
| 6,438,277 | B1 | 8/2002 | Eggleton et al. |
| 6,529,676 | B2 | 3/2003 | Eggleton et al. |
| 6,589,629 | B1 | 7/2003 | Bao et al. |
| 6,655,286 | B2 | 12/2003 | Rogers |
| 6,719,868 | B1 | 4/2004 | Schueller et al. |
| 6,736,985 | B1 | 5/2004 | Bao et al. |
| 6,743,982 | B2 | 6/2004 | Biegelsen et al. |
| 6,753,131 | B1 | 6/2004 | Rogers et al. |
| 6,769,769 | B2 | 8/2004 | Podoleanu et al. |
| 6,778,734 | B2 | 8/2004 | Baldwin et al. |
| 6,795,198 | B1 | 9/2004 | Fuchs et al. |
| 6,829,415 | B2 | 12/2004 | Kroupenkine et al. |
| 6,856,731 | B2 | 2/2005 | Rogers et al. |
| D502,993 | S | 3/2005 | McArthur et al. |
| 6,895,688 | B2 | 5/2005 | Acharya et al. |
| D508,565 | S | 8/2005 | Nephin et al. |
| 6,927,860 | B2 | 8/2005 | Podoleanu et al. |
| 6,943,998 | B2 | 9/2005 | Shimazawa et al. |
| 6,946,332 | B2 | 9/2005 | Loo et al. |
| 7,110,646 | B2 | 9/2006 | Eggleton et al. |
| 7,139,478 | B2 | 11/2006 | Eggleton et al. |
| 7,195,733 | B2 | 3/2007 | Rogers et al. |
| 7,199,699 | B1 | 4/2007 | Gidge |
| D545,441 | S | 6/2007 | Miyachika et al. |
| 7,229,541 | B2 | 6/2007 | Hara et al. |
| 7,229,847 | B2 | 6/2007 | Hsu et al. |
| D560,811 | S | 1/2008 | Powell et al. |
| D560,812 | S | 1/2008 | Powell et al. |
| D562,975 | S | 2/2008 | Otto |
| 7,330,213 | B2 | 2/2008 | Yamamoto |
| 7,330,273 | B2 | 2/2008 | Podoleanu et al. |
| 7,417,741 | B2 | 8/2008 | Podoleanu et al. |
| 7,439,096 | B2 | 10/2008 | Baldwin et al. |
| D582,560 | S | 12/2008 | Sachi |
| D583,955 | S | 12/2008 | Sachi |
| 7,521,292 | B2 | 4/2009 | Rogers et al. |
| 7,557,367 | B2 | 7/2009 | Rogers et al. |
| 7,704,684 | B2 | 4/2010 | Rogers et al. |
| 7,705,280 | B2 | 4/2010 | Nuzzo et al. |
| D618,810 | S | 6/2010 | Tanigawa et al. |
| 7,799,699 | B2 | 9/2010 | Nuzzo et al. |
| 7,943,491 | B2 | 5/2011 | Nuzzo et al. |
| D641,866 | S | 7/2011 | Burgess et al. |
| 8,372,726 | B2 | 2/2013 | De Graff et al. |
| D693,011 | S | 11/2013 | Mori et al. |
| D699,856 | S | 2/2014 | Mochizuki et al. |
| 8,734,339 | B2 | 5/2014 | Rao et al. |
| D719,267 | S | 12/2014 | Vaccarella |
| D730,761 | S | 6/2015 | Spaeth et al. |
| 9,061,494 | B2 | 6/2015 | Rogers et al. |
| 9,119,533 | B2 | 9/2015 | Ghaffari |
| 9,247,637 | B2 | 1/2016 | Hsu |
| D753,837 | S | 4/2016 | Sigurdsson et al. |
| 9,372,123 | B2 | 6/2016 | Li et al. |
| D762,869 | S | 8/2016 | Beckman et al. |
| D771,824 | S | 11/2016 | Minoli |
| D775,361 | S | 12/2016 | Vosch et al. |
| 9,545,285 | B2 | 1/2017 | Ghaffari et al. |
| 9,554,850 | B2 | 1/2017 | Lee et al. |
| 9,579,040 | B2 | 2/2017 | Rafferty et al. |
| 9,613,911 | B2 | 4/2017 | Rogers et al. |
| 9,622,680 | B2 | 4/2017 | Ghaffari et al. |
| 9,629,586 | B2 | 4/2017 | Ghaffari et al. |
| 9,702,839 | B2 | 7/2017 | Ghaffari et al. |
| 9,704,908 | B2 | 7/2017 | Graff et al. |
| 9,706,647 | B2 | 7/2017 | Hsu et al. |
| 9,723,122 | B2 | 8/2017 | Ghaffari et al. |
| 9,723,711 | B2 | 8/2017 | Elolampi et al. |
| 9,744,145 | B1 | 8/2017 | Liu et al. |
| 9,746,829 | B2 | 8/2017 | Stranczl et al. |
| D798,170 | S | 9/2017 | Toth et al. |
| 9,750,421 | B2 | 9/2017 | Ghaffari et al. |
| 9,757,050 | B2 | 9/2017 | Ghaffari et al. |
| 9,810,623 | B2 | 11/2017 | Ghaffari et al. |
| 9,833,190 | B2 | 12/2017 | Ghaffari et al. |
| 9,894,757 | B2 | 2/2018 | Arora et al. |
| 9,899,330 | B2 | 2/2018 | Dalal et al. |
| 9,949,691 | B2 | 4/2018 | Huppert et al. |
| D821,595 | S | 6/2018 | Ito et al. |
| 10,024,743 | B2 | 7/2018 | Gaboriault et al. |
| 10,032,709 | B2 | 7/2018 | Rafferty et al. |
| D825,537 | S | 8/2018 | Li et al. |
| D834,719 | S | 11/2018 | Theriot et al. |
| 10,161,737 | B2 | 12/2018 | Pegan et al. |
| 10,186,546 | B2 | 1/2019 | De Graff et al. |
| 10,192,830 | B2 | 1/2019 | Rogers et al. |
| D855,191 | S | 7/2019 | Hong et al. |
| D857,205 | S | 8/2019 | Lemons et al. |
| D863,562 | S | 10/2019 | Hahn |
| 10,485,463 | B2 | 11/2019 | Dietiker |
| 10,582,618 | B2 | 3/2020 | Coleman et al. |
| D886,303 | S | 6/2020 | Huang et al. |
| D894,422 | S | 8/2020 | Johnson |
| D896,391 | S | 9/2020 | Moriguchi |
| D898,924 | S | 10/2020 | Hinds et al. |
| D907,219 | S | 1/2021 | Neri |
| 10,898,084 | B2 | 1/2021 | Khine et al. |
| D928,974 | S | 8/2021 | Zulkosky et al. |
| 11,207,002 | B2 | 12/2021 | Khine et al. |
| D946,769 | S | 3/2022 | Stearns |
| D951,434 | S | 5/2022 | Boyaval et al. |
| 11,357,698 | B2 | 6/2022 | Baxter et al. |

(56) References Cited

U.S. PATENT DOCUMENTS

| | | | | |
|---|---|---|---|---|
| D961,093 | S | 8/2022 | Park | |
| D961,778 | S | 8/2022 | Mazza et al. | |
| D962,446 | S | 8/2022 | Bernstein et al. | |
| 11,464,451 | B1 | 10/2022 | Zavanelli et al. | |
| 11,660,005 | B1 | 5/2023 | Bolus | |
| D988,160 | S | 6/2023 | Morelock | |
| D1,002,019 | S | 10/2023 | Espinoza | |
| D1,006,997 | S | 12/2023 | Baxter et al. | |
| D1,013,544 | S | 2/2024 | Morelock | |
| D1,017,051 | S | 3/2024 | Fang et al. | |
| D1,022,244 | S | 4/2024 | Johnson | |
| D1,023,325 | S | 4/2024 | Aguiar et al. | |
| D1,035,004 | S | 7/2024 | Morelock | |
| D1,035,012 | S | 7/2024 | David et al. | |
| D1,036,676 | S | 7/2024 | Barry et al. | |
| D1,037,441 | S | 7/2024 | Brayman et al. | |
| D1,042,855 | S | 9/2024 | Moy et al. | |
| D1,048,908 | S | 10/2024 | Al-Ali et al. | |
| 12,109,010 | B1 | 10/2024 | Torstrick et al. | |
| 12,114,980 | B1 | 10/2024 | Torstrick et al. | |
| 12,178,552 | B1 | 12/2024 | Burnham et al. | |
| D1,057,169 | S | 1/2025 | Simmons et al. | |
| D1,067,424 | S | 3/2025 | Naughton et al. | |
| D1,068,516 | S | 4/2025 | Morelock | |
| D1,079,506 | S | 6/2025 | Park et al. | |
| D1,080,898 | S | 6/2025 | Mariotti | |
| D1,083,640 | S | 7/2025 | Morelock | |
| D1,094,766 | S | 9/2025 | Andersen et al. | |
| D1,112,768 | S | 2/2026 | Ehouarn et al. | |
| 12,575,741 | B1 | 3/2026 | Burnham et al. | |
| D1,123,167 | S | 4/2026 | VanHiel et al. | |
| D1,124,359 | S | 4/2026 | Aguirre | |
| D1,124,395 | S | 4/2026 | Duck et al. | |
| D1,126,422 | S | 5/2026 | Paschke et al. | |
| 2002/0180605 | A1 | 12/2002 | Ozguz et al. | |
| 2005/0096513 | A1 | 5/2005 | Ozguz et al. | |
| 2006/0276700 | A1* | 12/2006 | O'Neil | A61B 5/6841 600/323 |
| 2010/0292589 | A1 | 11/2010 | Goodman | |
| 2012/0084054 | A1 | 4/2012 | Yuen et al. | |
| 2013/0060109 | A1 | 3/2013 | Besko et al. | |
| 2014/0275845 | A1 | 9/2014 | Eagon | |
| 2014/0275888 | A1 | 9/2014 | Wegerich | |
| 2015/0305974 | A1 | 10/2015 | Ehrenreich et al. | |
| 2015/0351689 | A1* | 12/2015 | Adams | A61B 5/6833 600/300 |
| 2016/0302674 | A1 | 10/2016 | Moyer | |
| 2016/0313176 | A1 | 10/2016 | Lee | |
| 2017/0079144 | A1 | 3/2017 | Coleman et al. | |
| 2017/0156623 | A1 | 6/2017 | Chu et al. | |
| 2017/0347894 | A1 | 12/2017 | Bhushan et al. | |
| 2018/0177459 | A1 | 6/2018 | Eletr et al. | |
| 2019/0021616 | A1 | 1/2019 | Day et al. | |
| 2019/0069788 | A1 | 3/2019 | Coleman et al. | |
| 2019/0113326 | A1 | 4/2019 | Pegan et al. | |
| 2019/0133480 | A1 | 5/2019 | Rahman et al. | |
| 2019/0142625 | A1 | 5/2019 | Goff et al. | |
| 2019/0286233 | A1 | 9/2019 | Newberry | |
| 2019/0314192 | A1 | 10/2019 | Raj et al. | |
| 2020/0069193 | A1 | 3/2020 | Khine et al. | |
| 2020/0085336 | A1 | 3/2020 | Lu et al. | |
| 2020/0255791 | A1 | 8/2020 | Yeo et al. | |
| 2021/0000042 | A1 | 1/2021 | Birru et al. | |
| 2021/0059586 | A1* | 3/2021 | Marriott | A61B 5/7225 |
| 2021/0161405 | A1 | 6/2021 | Khine et al. | |
| 2022/0009764 | A1 | 1/2022 | Zhou et al. | |
| 2022/0280066 | A1 | 9/2022 | Chu et al. | |
| 2022/0296165 | A1 | 9/2022 | Datta et al. | |
| 2022/0322999 | A1 | 10/2022 | Clifford et al. | |
| 2023/0075040 | A1 | 3/2023 | Choe | |

FOREIGN PATENT DOCUMENTS

| | | | |
|---|---|---|---|
| EP | 3137038 | B1 | 12/2020 |
| EP | 3083248 | B1 | 4/2022 |
| EP | 3877830 | A1 | 8/2022 |
| EP | 3673797 | A1 | 6/2024 |
| WO | 2015095836 | A3 | 11/2015 |
| WO | 2015179320 | A1 | 11/2015 |
| WO | 2015179322 | A3 | 3/2016 |
| WO | 2017220526 | A1 | 12/2017 |
| WO | 2020092747 | A1 | 5/2020 |
| WO | 2020097505 | A1 | 5/2020 |
| WO | 2020228724 | A1 | 11/2020 |
| WO | 2020228725 | A1 | 11/2020 |
| WO | 2021055496 | A1 | 3/2021 |
| WO | 2021142121 | A1 | 7/2021 |
| WO | 2024191792 | A2 | 9/2024 |

OTHER PUBLICATIONS

Telfer, et al., Wearable Oximeby for Harsh Environments, IEEE, 2017, 4 pages.

U.S. Department of Health & Human Services. "Letter re: K162627, Trade/Device Name: EnsoSleep" Received by EnsoData, Inc., Mar. 31, 2017, 7 pages.

Zakeri, et al., Analyzing Seismocardiogram Cycles to Identify the Respiratory Phases, IEEE Transactions on Biomedical Engineering, Aug. 2017, 7 pages, vol. 64 No. 8.

Bicen, et al., A Signal Quality Index for Ballistocardiogram Recordings based on Electrocardiogram RR Intervals and Matched Filtering, IEEE EMBS International Conference on Biomedical & Health Informatics (BHI), Mar. 2018, 4 pages, Las Vegas.

Biometrics, et al., Medical electrical equipment—Part 2-61: Requirements for basic safety and essential performance of pulse oximeter equipment, International Standard, 2018, 100 pages, vol. 2.0, Geneva.

Hung, Central Sleep Apnea Detection Using an Accelerometer, Association for Computing Machinery, Jun. 2018, 6 pages.

Inan, et al., Novet Wearable Seismocardiography and Machine Leaming Algorithms Can Assess Clinical Status of Heart Failure Patients, Circ Heart Fail., 2018, 10 pages.

Jortberg, et al., a novet adhesive biosensor system for detecting respiration, cardiac, and limb movement signals during sleep: validation with polysomnography, Nature and Science of Sleep, 2018, 12 pages, vol. 10.

Liang, et al., Analysis: An optimal filler for short pholoplethysmogram signals, Scientific Data, May 2018, 12 pages.

Schlotthauer, et al., Measuring Complexity of Biomedical Signals, Hindawi Complexity, 2018, 4 pages, vol. 2018.

Sorensen, et al., Definition of Fiducial Points in the Normal Seismocardiogram, Scientific Reports, Oct. 2018, 11 pages.

Boe, et al., Automating sleep stage classification using wireless wearable sensors, npj Digital Medicine, 2019, 9 pages.

Budidha, et al., Photoplethysrnography for Quantitative Assessment of Sympathetic Nerve Activity (SNA) During Cold Stress, Front, Physiol, 9:1863, 2019, 10 pages, doi: 10.3389/fphys.2018.01863.

Choudhary, et al., Automatic Detection of Aortic Valve Opening Using Seismocarcliography in Healthy Individuals, IEEE Journal of Biomedical and Heal Th Informatics, May 2019, 9 pages, vol. 23, No. 3.

Dehkordi, et al., Comparison of Different Methods for Estimating Cardiac Timings: A Comprehensive Multimodal Echocardiography Investigation, Front. Physiol. 10:1057, Aug. 2019, 11 pages.

Gao, et al., Obstructive sleep apnea syndrome detection based on ballistocardiogram via machine learning approach, Mathematical Bioseiences and Engineering, Jun. 2019, 15 pages.

Ha et al., A Chest-Laminated Ultrathin and Stretchable E-Tattoo for the Measurement of Electrocardiogram, Seismocardiogram, and Cardiac Time Intervals, Advanced Science, 2019, 13 pages, vol. 6.

Hartmann, et al., Quantitative Comparison of Photoplethysmographic Waveform Characteristics: Effect of Measurement Site, front. Physiol., Mar. 2019, 8 pages.

(56) References Cited

OTHER PUBLICATIONS

Hossein, et al., Accurate Detection of Dobutamineinduced Haemodynamic Changes by Kino-Carcliography: A Randomised Double-Blind Placebo-Controlled Validation study, Scientific Reports, Jul. 2019, 11 pages.
Longmore, et al., A Comparison of Reflective Pholoplelhysmography for Detection of Heart Rate, Blood Oxygen Saturation, and Respiration Rate at Various Anatomical Locations, Sensors, Apr. 2019, 19 pages.
Morra, et al., Modification of the mechanical cardiac performance during end-expiratory voluntary apnea recorded with ballistocardiography and seismocardiography, Physiological Measurement, 2019, 32 pages.
Muthasamy, et al., An Overview of Respiratory Airflow Estimation Techniques: Acoustic vs Non-Acoustic, IEEE International Conference on Signal and Image Processing Applications, Sep. 2019, 5 pages.
Pandey, et al., Pulse Oximeter for Low Sp02 Levet Detection Using Discrete Time Signal Processing Algorithm, Journal of Medical Devices, Jun. 2019, 8 pages, vol. 18.
Taebi, et al., Recent Advances in Seismocardiography, Vibration, 2019, 23 pages, vol. 2.
Tamura, Current progress of photoplethysmography and SP02 for health monitoring, Biomedical Engineering Letters, Feb. 2019, 16 pages, vol. 9.
Tusman, et al., Pholoplelhysmographic characterization of vascular lone mediated changes in arterial pressure: an observational study, Journal of Clinical Monitoring and Computing, 2019, 10 pages, vol. 33.
FDA U.S. Food & Drug Administration. "Letter re: K202142, Trade/Device Name: Sleepware G3", Oct. 29, 2020, 9 pages.
Ganti, et al., Wearable Cuff-less Blood Pressure Estimation at Home via Pulse Transit Time, IEEE Journal of Biomedical and Health Informatics, 2020, 12 pages.
Gupta, et al., Precision wearable accelerometer contact microphones for longitudinal monitoring of mechano-acoustic pardiopulmonary signals, npj Digital medicine, 2020, 8 pages.
Hsu, et al., Screening of obstructive sleep apnea in patients who snore using a patch-type device with electrocardiogram and 3-axis accelerometer, Journal of Clinical Sleep Medicine, 2020, 12 pages.
Klum, et al., Wearable Cardiorespiratory Monitoring Employing a Multimodal Digital Patch Stethoscope: Estimation of ECG, PEP, LVET and Respiration Using a 55 mm Single-Lead ECG and Phonocardiogram, Sensors, Apr. 2020, 21 pages, vol. 20.
Morra, et al., Ballistocardiography and Seismocardiography detect hemodynamic changes during simulated obstructive apnea, Physiological Measurement, 2020, 34 pages.
Munck, et al., Multichannet seismocardiography: an imaging modality for investigating heart vibrations, Physiological Measurement, 2020, 12 pages, vol. 41.
Racape, et al., Influence of sympathetic activation on myocardial contractility measured with ballistocardiography and seismocardiography during sustained end-expiratory apnea, Am J Physiol Regul Integr Comp Physiol, Sep. 2020, 10 pages.
Semiz, et al., Non-Invasive Wearable Patch Utilizing Seismocardiography for Peri-Operative Use in Surgical Patients, IUEEE, 2020, 11 pages.
Skoric, et al., Relationship of the Respiration Waveform to a Chest Worn Inertial Sensor, IEEE, 2020, 4 pages.
FDA U.S. Food & Drug Administration. Letter re: 1<210034, Trade/Device Name: EnsoSleep . . . , May 2021, 24 pages.
Kwon, et al., Recent advances in wearable sensors and portable electronics for sleep monitoring, iScience, May 2021, 16 pages, vol. 24.
"510(k) Premarket Notification." Accessdata.fda.gov, U.S. Department of Health & Human Services, Aug. 22, 2022, https://www.accessdata.fda.gov/scripts/cdrh/cfdocs/cfpmn/pmn.cfm?l.
FDA U.S. Food & Drug Administration. aLetter re: 1<213007, Trade/Device Name: Cerebra Sleep System . . . , Jul. 6, 2022, 17 pages.
Davies, Charles, et al., "A Single Arm, Open-Label, Multi-Center, and Comparative Study of the ANNE Sleep System versus Polysomnography to Diagnose Obstructive Sleep Apnea." Journal of Clinical Sleep Medicine : JCSM : Official Publication of the American Academy of Sleep Medicine, U.S. National Library of Medicine, https://pubmed.ncbi.nlm.nih.gov/35934926/.
Razjouyan, et al., Improving Sleep Quality Assessment Using Wearable Sensors by Including Information From Postural/Sleep Position Changes and Body Acceleration: A Comparison of Chest-Worn Sensors, Wrist Actigraphy, and Polysomnography, Journal of Clinical Sleep Medicine, 2017, 10 pages, vol. 13 No. 11.
Budidha, et al., Investigation of Pulse Transit Times utilizing multisite reflectance photoplethysmography under conditions of artificially induced peripheral vasoconstriction. 2014 36th Annual International Conference of the IEEE Engineering in Medicine and Biology Society (EMBC), pp. 1965-1968. doi: 10.1109/EMBC.2014.6943998.
Mendelson, et al., Noninvasive Pulse Oximetry Utilizing Skin Reflectance Photoplethysmography, IEEE Transactions on Biomedical Engineering, Oct. 1988, 8 pages, vol. 35 No. 10.
Rusch, et al., Alternate Pulse Oximetry Algorithms for Sp02 Computation, University of South Florida, 1994, 2 pages.
Rusch, et al., Signal Processing Methods for Pulse Oximetry, Comput. Biol. Med., Oct. 1995, 17 pages, vol. 26 No. 2.
Dassel, et al., Effect of location of the sensor on reflectance pulse oximetry, British Journal of Obstetrics and Gynaecology, Aug. 1997, pp. 910-916, vol. 104.
Goldman, et al., Masirno Signal Extraction Pulse Oximetry, Journal of Clinical Monitoring and Computing, Jan. 2000, 9 pages, vol. 16, Kluwer Academic Publishers, Netherlands.
Clifford, et al., Signal Processing Methods for Heart Rate Variability, St. Cross College, 2002, 244 pages.
Graybeal, et al., Adaptive Filtering and Alternative Calculations Revolutionizes Pulse Oximetry Sensitivity and Specificity During Motion and Low Perfusion, IEEE EMBS, Sep. 2004, 4 pages.
Johnston, Development of a Signal Processing Library for Extraction of SpO2, HR, HRV, and RR from Photoplethysmographic Waveforms, Worcester Polytechnic Institute, 2006, 148 pages.
Morillo, et al., Monitoring and Analysis of Cardiorespiratory and Snoring Signals by using an Accelerometer, IEEE EMBS, Aug. 2007, 4 pages.
Nilsson, et al., Combined photoplethysmographic monitoring of respiration rate and pulse: a comparison between different measurement sites in spontaneously breathing subjects, Acta Anaesthesiol Scand, 2007, 8 pages, vol. 51.
Sola, et al., On the reliability of pulse oximetry at the sternum, IEEE EMBS, Aug. 2007, 1 page.
Hung, et al., Estimation of Respiratory Waveform Using an Accelerometer, IEEE ISBI, 2008, 4 Pages.
Tilmanne, et al., Algorithms for sleep-wake identification using acligraphy: a comparative study and new results, European Sleep Research Society, Sep. 2008, 14 pages.
Barker, Signal Extraction Technology, Nov. 30, 2009, 45 pages.
Etemadi, et al., Non-Invasive Assessment of Cardiac Contractility on a Weighing Scale, IEEE EMBS, Sep. 2009, 4 pages.
Jensen, Signal Processing of Nano Sensor Data, Kongens Lyngby, Mar. 2009, 127 pages.
Jensen, et al., Independent Component Analysis Applied to Pulse Oximelry in the Estimation of the Arterial Oxygen Saturation {SpO2)—a Comparative Study, IEEE Embs, Sep. 2009, 7 pages.
Vetter, et al., Frequency Domain SpO2 Estimation Based on Multichannet Photoplethysmographic Measurements the Sternum, IFMBE Proceedings, 2009, 4 pages, vol. 25.
Bsoul, et al., Real-Time Sleep Quality Assessment Using Single-Lead ECG and Multi-Stage SVM Classifier, IEEE, Sep. 2010, 4 pages, Buenos Aires.
Inan, et al., Evaluating the Lower-Body Electromyogram Signal Acquired from the Feet As a Noise Reference for Standing Ballistocardiogram Measurements, IEEE Transactions on Information Technology in Biomedicine, Sep. 2010, 9 pages, vol. 14 No. 5.
Morillo, et al., An Accelerometer-Based Device for Sleep Apnea Screening, IEEE Transactions on Information Technology in Biomedicine, Mar. 2010, 9 pages, vol. 10 No. 2.

(56) References Cited

OTHER PUBLICATIONS

Pandia, et al., Motion Artifact Cancellation to Obtain Heart Sounds From a Single Chestworn Accelerometer, IEEE ICASSP, 2010, 4 pages.
Tavakolian, Characterization and Analysis of Seismocardiogram for Estimation of Hemodynamic Parameters, Simon Fraser University, Fall 2010, 217 pages.
Bsoul, et al., Apnea MedAssist Real-time Sleep Apnea Monitor Using Single-Lead ECG, IEEE Transactions on Information Technology in Biomedicine, May 2011, 12 pages, vol. 15.
Li, et al., Principle Component Analysis on Photoplethysmograms: Blood Oxygen Saturation Estimation and Signal Segmentation, IEEE EMBS, Sep. 2011, 4 pages.
Sola, et al., Chest Pulse-Wave Velocity: A Novet Approach to Assess Arterial Stiffness, IEEE Transactions on Biomedical Engineering, Jan. 2011, 9 pages, vol. 58 No. 1.
Younes Sleep Technologies. "Traditional 510(k) Summary K112102 Michelle Sleep Scoring System." Oct. 16, 2011, 16 pages.
Castiglioni, et al., Seisrnocarcliography While Sleeping at High Altitude, IEEE EMBS, Aug. 2012, 4 pages.
Clifford, et al., Signal quality in cardiorespiratory monitoring, Physiol. Meas. 33 E01, 2012, 6 pages.
Haahr, et al., An Electronic Patch for Wearable Health Monitoring by Reflectance Pulse Oximetry, IEEE Transactions on Biomedical Circuits and Systems, Feb. 2012, 9 pages, vol. 6 No. 1.
Pandia, et al., Extracting respiratory information from seismocardiogram signals acquired on the chest using a miniature accelerometer, Physiological Measurement, Sep. 2012, 19 pages, vol. 33.
Di Rienzo, et al., Wearable seismocardiography: Towards a beat-by-beat assessment of cardiac mechanics in ambulant subjects, Autonomic Neuroscience: Basic and Clinical, Apr. 2013, 10 pages.
Pandia, et al., A Frequency Domain Analysis of Respiratory Variations in the Seismocardiogram Signal, IEEE EMBS, Jul. 2013, 4 pages.
He, et al., Secondary Peak Detection of PPG Signal for Continuous Cuffless Artenal Blood Pressure Measurement, IEEE Transactions on Instrumentation and Measurement, Jun. 2014, 9 pages.
Inan, et al., Ballistocarcliography and Seismocarcliography: A Review of Recent Advances, IEEE Journal of Biomedical and Heal Th Informatics, 2014, 30 pages.
Nara, et al., Novet Notch Detection Algorithm for Detection of Dicrotic Notch in PPG Signals, International Journal of Computer Applications, Jan. 2014, 5 pages, vol. 86 No. 17.
Broser, et al., Ambient and Unobtrusive Cardiorespiratory Monitoring Techniques, IEEE Reviews in Biomedical Engineering, 2015, 14 pages, vol. 8.
Budidha, et al., Investigation of photoplethysmography and arterial blood oxygen saturation from the ear-canal and the finger under conditions of artificially induced hypothermia, IEEE Engineering in Medicine and Biology Society Conference, Aug. 2015, 5 pages.
Fonseca, et al., Sleep stage classification with ECG and respiratory effort, Physiological Measurement, 2015, 15 pages, vol. 36.
U.S. Department of Health & Human Services. "Letter re: K142988, Trade/Device Name: Sleepware G3 . . . ", Mar. 16, 2015, 8 pages.
Chreiteh, Investigation of Sternal Photoplelhysmography—Design of a Vital Sign Patch, Technical University of Denmark, Mar. 2016, 187 pages.
Etemadi, et al., A Wearable Patch to Enable Long-Term Monitoring of Environmental, Activity and Hemodynamics Variables, IEEE Transactions on Biomedical Circuits and Systems, 2016, 9 pages.
Javaid, et al., Quantification of Posture Induced Changes in Wearable Seismocardiogram Signals for Heart Failure Patients, Computing in Cardiology, 2016, 4 pages, vol. 43.
Zheng, et al., Low Ferfusion Algorithm used in Wearable Oximeter and Hardware Acceleration, IEEE, 2016, 5 pages.
Carek, et al., SeismoWatch: Wearable Cuffless Blood Pressure Monitoring Using Pulse Transit Time, Proc. ACM Interact. Mob. Wearable Ubiquitous Technol. 1, 3, Article 40, Sep. 2017, 16 pages.
Etemadi, et al., Wearable Ballistocardiogram and Seismocardiogram Systems for Health and Performance, Press. J Appl Physiol, Aug. 2017, 35 pages.
Inan, Wearable Sensing of Left Ventncular Function, Spring International Publishing, Mobile Health, 2017, 23 pages.
Javaid, et at, Quantifying and Reducing Motion Artifacts in Wearable Seismocardiogram Measurements during Walking to Assess Left Ventricular Health, IEEE TBME, 2017, 9 pages.
Khosrow-Khavar, et al., Automatic and Robust Delineation of the Fiducial Points of the Seismocardiogram Signal for Noninvasive Estimation of Cardiac Time Intervals, IEEE Transactions on Biomedical Engineering, Aug. 2017, 10 pages, vol. 64. No. 8.
Kramer, et al., Wearable Pulse Oximetry Measurements on the Torso, Arms, and Legs: A Proof of Concept, Military Medicine, 2017, 7 pages.
"OB1203 Pulse Oximeter Algorithm for SpO2, Heart Rate, and Respiration Rate ", Renesas, Retrieved from: https://www.renesas.com/en/document/apn/ob1203-pulse-oximeter-algorithm-spo2-heart-rate-and-respiration-rate?srsltid=AfmBOoqrkM4I-MhD_7qsZ89-BrNjjNek5soVT2ifdL91X_RKPY8IUnqF, Apr. 25, 2022, 16 pages.

* cited by examiner

PHOTOPLETHYSMOGRAPHY SENSORS AND PROCESSES

CROSS-REFERENCE TO RELATED APPLICATIONS

This application is a continuation of U.S. patent application Ser. No. 17/821,990, filed Aug. 24, 2022, entitled "PHOTOPLETHYSMOGRAPHY SENSORS AND PROCESSES," which claims priority to U.S. Provisional Patent Application No. 63/236,511, filed Aug. 24, 2021, entitled "PHOTOPLETHYSMOGRAPHY SENSORS AND PROCESSES," each of which are incorporated herein by reference in their entireties.

GOVERNMENT LICENSE RIGHTS

This invention was made with government support under NSF Award ID 2136470 awarded by the National Science Foundation. The government has certain rights in the invention.

BACKGROUND

Photoplethysmography (PPG) generally refers to light-based techniques for detecting volumetric changes in blood. Typically, PPG is performed by directing an input light source at a subject's skin, measuring an amount of light reflected and/or transmitted by the skin, and determining a biological signal (e.g., heart rate variance, dissolved oxygen, etc.) based on the amount of light measured. Previous approaches to performing PPG have relied on large sensing units that include multiple arrays of light-emitting elements (e.g., LEDS) and light-detecting elements (e.g., photodiodes). Such systems typically rely on large sensing footprints and redundant sensing elements to compensate for natural and motion-induced variations in skin surface especially for reflectance PPG. For example, a sleeping subject rotates from a first side to a second side, thereby shifting and warping skin surfaces and, thus, changing the light reflection and transmission behavior of the skin. In this example, past approaches may attempt to accommodate changes in skin surface by measuring signals over a large surface area via a multitude of PPG arrays.

Consequently, previous PPG sensing systems demonstrate large spatial profiles (e.g., due to sensing area requirements) and high complexity (e.g., due to multiple PPG arrays). Large spatial profiles and high complexity are undesirable for biological signal sensors and, especially so, for sensors intended to be actively worn by a subject. For example, highly complex PPG sensing systems may be cost prohibitive, difficult to calibrate, and unaccommodating of subject motion. Furthermore, PPG sensing systems with large spatial profiles may be unsuitable for everyday use outside of a clinical setting and/or for subjects with physical dimensions that fall outside of a typical or expected range.

Therefore, there exists a long felt but unmet need for motion-tolerant, low profile PPG sensing systems.

BRIEF DESCRIPTION OF THE DISCLOSURE

There are various factors that may influence quality and/or repeatability of PPG signals of a device worn on a patient's chest (and other locations). These factors include, but may not be limited to: 1) skin axial strain; 2) skin shear strain; 3) skin bending (or folding/buckling); 4) PPG sensor tilting; 5) skin contact (or potential loss of skin contact); 6) anatomy (e.g., bone, muscle, fat, arterial, venous, hair, body mass index (BMI), etc.); 7) blood pressure; 8) melanin pigmentation; and 9) local perfusion state. As will be discussed, various embodiments of the systems and processes discussed herein mitigate these potential factors by at least: a) strain isolation of the PPG sensor with a large (relative to the PPG sensor), rigid enclosure (helps mitigate skin strain and bending factors); b) conformality (elastic spacer-helps maintain constant skin contact); and c) load (helps maintain skin contact even with PPG sensor tilting and overcomes anatomical issues by applying pressure that matches or exceeds diastolic pressure to minimize the effect of venous or deoxygenated blood content).

According to a first aspect, a patch including: a silicon-based adhesive layer defining a silicon-based adhesive layer opening and including a first side and a second side; an acrylic-based adhesive layer connected to the first side of the silicon-based adhesive layer, wherein the acrylic-based adhesive layer is exposed on the second side of the silicon-based adhesive layer through the opening; a rigid support structure including a bottom surface area defining a rigid support structure opening for a photoplethysmography (PPG) system; and the PPG system extending through the rigid support structure opening and including: a first side and a second side; and a spacer operatively connected to the first side of the PPG sensor, wherein when the patch is attached to a patient's skin: the silicon-based adhesive layer attaches to a first portion of the patient's skin; the acrylic-based adhesive layer attaches to a second portion of the patient's skin, the second portion of the patient's skin corresponding to at least a portion of the bottom surface area of the rigid support structure extending through the silicon-based adhesive layer opening; and the acrylic-based adhesive layer attaches to a third portion of the patient's skin, the third portion of the patient's skin corresponding to an area of the acrylic-based adhesive layer in contact with the PPG sensor.

According to a second aspect, the patch of the first aspect or any other aspect, wherein the patch includes a vertical distance between the second side of the PPG sensor and the bottom surface area of the rigid support structure.

According to a third aspect, the patch of the second aspect or any other aspect, wherein, when attached to the patient's skin, the second side of the PPG sensor is pressed into the patient's skin.

According to a fourth aspect, the patch of the third aspect or any other aspect, wherein an amount of pressure exerted by the patch on the patient when the PPG sensor is pressed into the patient's skin is at least partially based on the vertical distance.

According to a fifth aspect, the patch of the fourth aspect or any other aspect, wherein the vertical distance is 10 mm or less.

According to a sixth aspect, the patch of the first aspect or any other aspect, wherein the spacer is elastic.

According to a seventh aspect, the patch of the sixth aspect or any other aspect, wherein the spacer is silicone.

According to an eighth aspect, the patch of the seventh aspect or any other aspect, wherein the spacer is porous.

According to a ninth aspect, the patch of the first aspect or any other aspect, further including a flexible printed circuit board (PCB) connected to first side of PPG sensor.

According to a tenth aspect, the patch of the ninth aspect or any other aspect, wherein the PCB collects signal data from the PPG sensor.

According to an eleventh aspect, the patch of the tenth aspect or any other aspect, wherein the patch further transmits data from the PPG sensor to a computing system.

According to a twelfth aspect, a patch including: a first adhesive area; a second adhesive area adjacent to the first adhesive area; a rigid support structure including a bottom surface; a strain isolation area including at least a portion of the second adhesive area supported by the rigid support structure; and a photoplethysmography (PPG) sensor operatively connected to the rigid support structure including: a first side and a second side; and an elastic spacer operatively connected to the first side of the PPG sensor; a vertical distance between the bottom surface of the rigid support structure and the second side of the PPG sensor; a PPG area including the second side of the PPG sensor and a portion of the second adhesive area, wherein: the PPG sensor tilts with respect to the rigid support structure via the elastic spacer; and the strain isolation area surrounds the PPG area.

According to a thirteenth aspect, the patch of the twelfth aspect or any other aspect, wherein the PPG sensor is pressed into a patient's skin based at least in part on the vertical distance between the bottom surface of the rigid support structure and the second side of the PPG sensor.

According to a fourteenth aspect, the patch of the thirteenth aspect or any other aspect, wherein the amount of pressure exerted by the patch on the patient when the PPG sensor is pressed into the patient's skin is at least partially based on the vertical distance.

According to a fifteenth aspect, the patch of the fourteenth aspect or any other aspect, wherein the vertical distance is 10 mm or less.

According to a sixteenth aspect, the patch of the fifteenth aspect or any other aspect, wherein the PPG sensor tilts with respect to the rigid support structure via the elastic spacer, thereby creating conformal contact between the second side of the PPG sensor and the patient's skin when the PPG sensor is pressed into the patient's skin.

According to a seventeenth aspect, the patch of the sixteenth aspect or any other aspect, wherein: the patch includes a first adhesive layer; and the first adhesive area includes at least a portion of an adhesive side of the first adhesive layer.

According to a eighteenth aspect, the patch of the seventeenth aspect or any other aspect, wherein: the patch includes a second adhesive layer; and the second adhesive area includes at least a portion of an adhesive side of the second adhesive layer.

According to a nineteenth aspect, the patch of the eighteenth aspect or any other aspect, wherein: the second adhesive layer includes a non-adhesive side; and the second side of the PPG sensor contacts the non-adhesive side of the second adhesive layer.

According to a twentieth aspect, the patch of the nineteenth aspect or any other aspect, wherein: the PPG sensor extends through an opening formed by the bottom surface of the rigid support structure; and the elastic spacer is operatively connected to the rigid support structure.

According to a twenty-first aspect, patch for obtaining PPG signals from low perfusion anatomical sites including: a first adhesive layer defining an opening; a photoplethysmography (PPG) system including: a PPG sensor including a first side and a second side; a spacer operatively connected to a first side of the PPG sensor; a second adhesive layer in contact with the second side of the PPG sensor, the second adhesive layer and the second side of the PPG sensor extending through the opening; and a distance between an edge of the opening and the PPG sensor extending therethrough, wherein the PPG sensor is strain isolated based at least in part on distance.

According to a twenty-second aspect, the patch of the twenty-first aspect or any other aspect, wherein the patch further includes a vertical distance between a surface of the first adhesive layer and the second side of the PPG sensor.

According to a twenty-third aspect, the patch of the twenty-second aspect or any other aspect, wherein: the patch is for attaching to a patient's skin via the first adhesive layer and the second adhesive layer; and the patch presses the second side of the PPG sensor into the patient's skin based at least in part on the vertical distance.

According to a twenty-fourth aspect, the patch of the twenty-third aspect or any other aspect, wherein the spacer is elastic.

According to a twenty-fifth aspect, the patch of the twenty-third aspect or any other aspect, wherein: the patch includes a support structure operatively connected to the spacer; and the spacer enables the PPG sensor to tilt with respect to the support structure, creating conformal contact with the patient's skin.

According to a twenty-sixth aspect, the patch of the twenty-fifth aspect or any other aspect, wherein the spacer is porous.

According to a twenty-seventh aspect, the patch of the twenty-sixth aspect or any other aspect, wherein the second adhesive layer is stronger than the first adhesive layer.

According to a twenty-eighth aspect, the patch of the twenty-seventh aspect or any other aspect, wherein the first adhesive layer is a silicon-based adhesive layer.

According to a twenty-ninth aspect, the patch of the twenty-eighth aspect or any other aspect, wherein the second adhesive layer is an acrylic-based adhesive layer.

According to a thirtieth aspect, the patch of the twenty-ninth aspect or any other aspect, or of any other claim, wherein the patch presses the second side of the PPG sensor into the patient's skin based at least in part on the vertical distance at a pressure of about 80-120 mm Hg, thereby minimizing effects of venous or deoxygenated blood content on PPG readings.

According to a thirty-first aspect, a patch including: a strain isolation zone including a first layer and a rigid support structure, the strain isolation zone surrounding a photoplethysmography (PPG) zone, wherein the first layer includes an adhesive side and a non-adhesive side; the PPG zone including the first layer and a PPG sensor, wherein the PPG sensor is in contact with the non-adhesive side of the first layer; and a contact zone surrounding the strain isolation zone and including a second layer, the second layer forming an opening thereby exposing the first layer and the PPG sensor therethrough.

According to a thirty-second aspect, the patch of the thirty-first aspect or any other aspect, wherein the second layer includes an adhesive side.

According to a thirty-third aspect, the patch of the thirty-second aspect or any other aspect, wherein the second layer adhesive side includes a weaker adhesive than the first layer adhesive side.

According to a thirty-fourth aspect, the patch of the thirty-third aspect or any other aspect, wherein the patch is for attaching to a patient's skin via the second layer adhesive side and the first layer adhesive side.

According to a thirty-fifth aspect, the patch of the thirty-fourth aspect or any other aspect, wherein the patch includes a vertical distance between the PPG sensor and the second layer adhesive side.

According to a forty-first aspect, a patch including: a strain isolation zone including a strain isolation adhesive and a rigid support structure, the strain isolation zone surrounding a photoplethysmography (PPG) zone; the PPG zone including a PPG sensor and a PPG adhesive; and a contact zone surrounding the strain isolation zone and including a contact zone adhesive, the contact zone adhesive forming an opening thereby exposing the strain isolation zone and the PPG zone.

According to a forty-second aspect, the patch of the forty-first aspect or any other aspect, wherein the patch is configured for attaching to skin of a patient.

According to a forty-third aspect, the patch of the forty-second aspect or any other aspect, wherein the patch includes a spacer operatively connected to the rigid support structure and the PPG sensor.

According to a forty-fourth aspect, the patch of the forty-third aspect or any other aspect, wherein the spacer is elastic.

According to a forty-fifth aspect, the patch of the forty-fourth aspect or any other aspect, wherein the patch includes a vertical distance between a first end of the PPG sensor and the contact zone adhesive.

According to a forty-sixth aspect, the patch of the forty-fifth aspect or any other aspect, wherein the PPG zone exerts is a force into the skin of the patient based at least in part on the vertical distance.

According to a forty-seventh aspect, the patch of the forty-sixth aspect or any other aspect, wherein the strain isolation zone pulls the skin of the patient towards the rigid support structure.

According to a forty-eighth aspect, the patch of the forty-seventh aspect or any other aspect, wherein the strain isolation adhesive is a stronger adhesive than the contact zone adhesive.

According to a forty-ninth aspect, the patch of the forty-eighth aspect or any other aspect, wherein the patch includes a first layer including the strain isolation adhesive and the PPG adhesive.

According to a fiftieth aspect, the patch of the forty-ninth aspect or any other aspect, wherein the patch includes a second layer including the contact layer adhesive.

According to a fifty-first aspect, the patch of the fiftieth aspect or any other aspect, wherein: the first layer is connected to the second layer; and the first layer and the first end of the PPG sensor extend through the opening.

According to a sixty-first aspect, a process for obtaining PPG data including: creating a strain isolation zone on a patient's skin by attaching a strain isolation adhesive backed by a rigid support structure to the patient's skin, the strain isolation zone surrounding a photoplethysmography (PPG) zone; creating the PPG zone by attaching a PPG adhesive to the patient's skin, the PPG adhesive backed by a PPG sensor; and creating a contact zone surrounding the strain isolation zone by attaching a contact zone adhesive to the patient's skin, the contact zone adhesive surrounding the strain isolation zone and the PPG zone.

According to a sixty-second aspect, the process of the sixty-first aspect or any other aspect, wherein the strain isolation adhesive is a stronger adhesive than the contact zone adhesive.

According to a sixty-third aspect, the process of the sixty-second aspect or any other aspect, wherein the patch includes a first layer including the strain isolation adhesive and the PPG adhesive.

According to a sixty-fourth aspect, the process of the sixty-third aspect or any other aspect, wherein the patch includes a second layer including the contact layer adhesive.

According to a sixty-fifth aspect, the process of the sixty-fourth aspect or any other aspect, wherein the first layer is connected to the second layer.

According to a sixty-sixth aspect, the process of the sixty-fifth aspect or any other aspect, wherein the first layer and at least a portion of the PPG sensor extend through an opening formed by the second layer.

According to a sixty-seventh aspect, the process of the sixty-fifth aspect or any other aspect, wherein the patch includes a spacer operatively connected to the PPG sensor.

According to a sixty-eighth aspect, the process of the sixty-seventh aspect or any other aspect, wherein the spacer is elastic.

According to a sixty-nineth aspect, the process of the sixty-first aspect or any other aspect, wherein the patch includes a vertical distance between a first end of the PPG sensor and the contact zone adhesive.

According to a seventieth aspect, the process of the sixty-nineth aspect or any other aspect, wherein the PPG zone exerts is a force into the skin of the patient based at least in part on the vertical distance.

According to a seventy-first aspect, the process of the seventieth aspect or any other aspect, wherein the strain isolation zone pulls the skin of the patient towards the rigid support structure.

According to a seventy-second aspect, a patch or process of any other aspect, wherein: the PPG sensor is a first PPG sensor; the rigid support structure opening is a first rigid support structure opening; the rigid support structure includes one or more second support structure openings; the patch includes: one or more second PPG sensors; and a force sensor associated with the first PPG sensor and/or the one or more second PPG sensors; the one or more second PPG sensors extend through the one or more second support structure openings; each of the first PPG sensor and the one or more second PPG sensors exert a different force on a patient's skin.

Third-party systems fail to provide the ability to observe and monitor a variety of subject data points. Additionally, they fail to provide a single device attached at one location on a subject to observe each of these data points. The present disclosure provides for a single patch for monitoring and retrieving a plurality of data points from a subject. Additionally, the present disclosure provides a method and system for calculating and evaluating those various biometric data points while also detecting disorders of a subject associated with such data.

Using the processes and systems as disclosed, a provider may be able to easily identify issues associated with a subject and provide a diagnosis. Sleep apnea, and other breathing disorders, are common among subjects, and through the use of the processes and systems of the present disclosure, these disorders can be more easily and with more accuracy be diagnosed and treated.

Figure 1A:
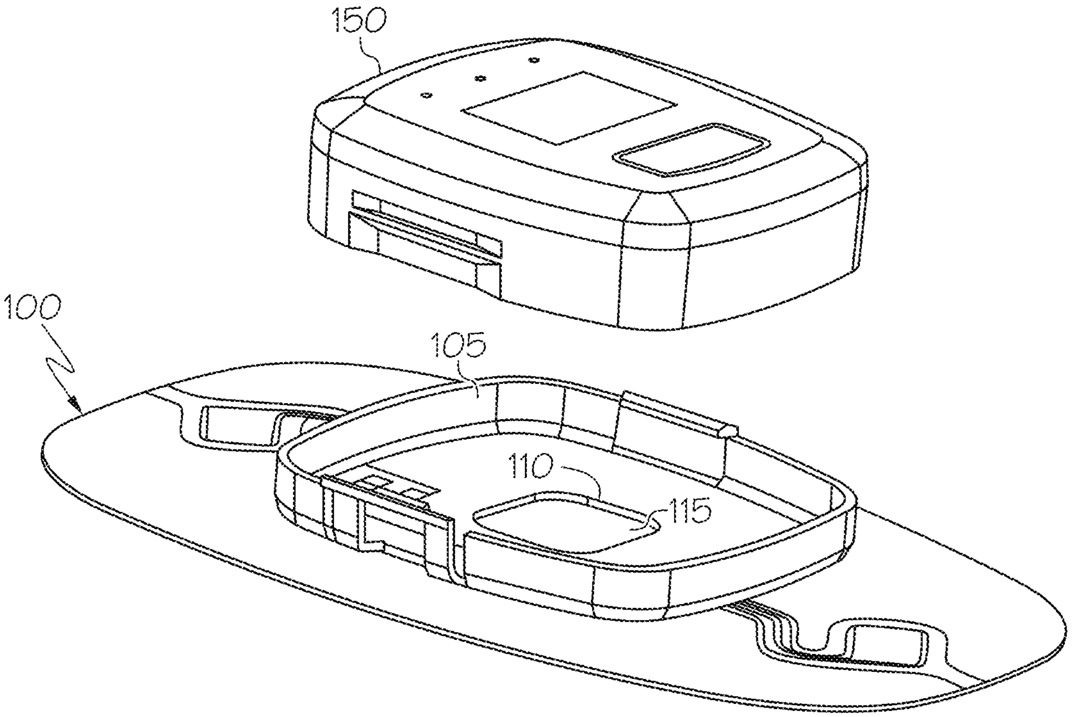
FIG. 1A illustrates a first perspective view of an example patch device according to various embodiments of the present disclosure.

While the disclosure is susceptible to various modifications and alternative forms, a specific embodiment thereof is shown by way of example in the drawings and will herein be described in detail. It should be understood, however, that the drawings and detailed description presented herein are not intended to limit the disclosure to the particular embodiment disclosed, but to the contrary, the intention is to cover all modifications, equivalents, and alternatives falling within the spirit and scope of the present disclosure as defined by the appended claims.

DETAILED DESCRIPTION

Aspects, features, and benefits of the systems, methods, processes, formulations, apparatuses, and products discussed herein will become apparent from the information disclosed herein and in the other application incorporated by reference. Variations and modifications to the disclosed systems and methods may be effected without departing from the spirit and scope of the novel concepts of the disclosure.

It will, nevertheless, be understood that no limitation of the scope of the disclosure is intended by the information disclosed herein or in the application incorporated by reference; any alterations and further modifications of the described or illustrated embodiments, and any further applications of the principles of the disclosure as illustrated therein are contemplated as would normally occur to one skilled in the art to which the disclosure relates.

According to various embodiments, aspects of the present disclosure generally relate to systems and apparatuses for deriving improved PPG signals. In one or more embodiments, the described PPG devices are configured to emit light against a subject's skin, measure a magnitude of light reflected from and/or transmitted through the subject's skin, and, based on the magnitude of light measured, determine one or more biological signals of the subject.

In one example, an embodiment of the present PPG device is affixed to a subject's skin and records reflected light intensities throughout the subject's sleep cycle. In the same example, based on the recorded intensities, the PPG device (or connected systems) determine, derive or estimate a variety of parameters and factors of the subject, including, but not limited to, the subject's dissolved oxygen (SpO2) level, heart rate variability (HRV), pulse rate, and blood pressure, which may be used to monitor the subject's health and/or support evaluation of the subject for one or more conditions (e.g., sleep apnea and other sleep-related disorders). In one or more embodiments, the present PPG devices provide advantages including, but not limited to, low spatial profile, high tolerance to subject motion, greater signal amplitude on low perfusion anatomical sites, and compatibility with any skin tone or pigment.

For example, in contrast to previous approaches that require numerous and outsized light sensing arrays, the PPG solution presented herein may operate with a single PPG array that demonstrates a minimal spatial footprint. As another example, past approaches typically require redundant PPG sensing units to compensate for losses in signal quality at one or more PPG sensing elements during skin strain and deformation (e.g., as caused by subject motion, clothing, or external phenomena) or on low perfusion anatomical sites. In contrast, the present PPG solution may operate with a single PPG sensing unit that tolerates subject motion, clothing, and other external phenomena without experiencing significant losses in accuracy and precision. The present PPG solution may also function on low perfusion anatomical sites.

FIG. 1A illustrates a first perspective view of an example patch device according to various embodiments of the present disclosure.

According to various embodiments, the patch device includes a patch 100 and a pod 150. In one embodiment, the patch 100 includes a cradle 105. According to some embodiments, the pod 150 attaches to the patch 100 via a latch on the cradle 105. As will be understood from discussions herein, the patch 100 and pod 150 may be one integrally formed device or may be split into more components than shown in FIG. 1A. As will also be understood, patch 100 and pod 150 may connect via any suitable mechanism not shown (e.g., a suitable adhesive or the like).

The cradle 105 may include an opening 110. In various embodiments, the opening 110 is generally a rectangular shape with rounded corners. In at least one embodiment, the opening 110 is any suitable shape, such as, but not limited to, circular, ovoid, square, etc. According to one embodiment, the opening 110 receives a PPG sensor and may be shaped to receive the PPG sensor. In at least one embodiment, the opening is generally a square shape (with rounded corners) and each side of the square is about 16-20 mm.

The cradle 105 may be constructed of any suitable material. In at least one embodiment, the cradle 105 is constructed of a stiff material (or materials), including any suitable plastic material.

As shown in FIG. 1A, the patch 100 includes a second adhesive 130 (FIG. 1B), which spans the [0098] opening 110. In these embodiments (and others), the patch 100 includes a top side 115 of a second adhesive layer 130 seen through opening 110 (as further described with reference to FIG. 1B). As will be understood, the second adhesive layer 130 (as seen through opening 110) may be part of a larger adhesive layer that spans a portion of the patch 100 or may be an adhesive layer for covering opening 110 (and/or an additional small portion of the patch 100). As will also be understood, the adhesive layer 130 may include a non-adhesive side shown in FIG. 1A and an adhesive side shown in FIG. 1B.

Figure 1B:
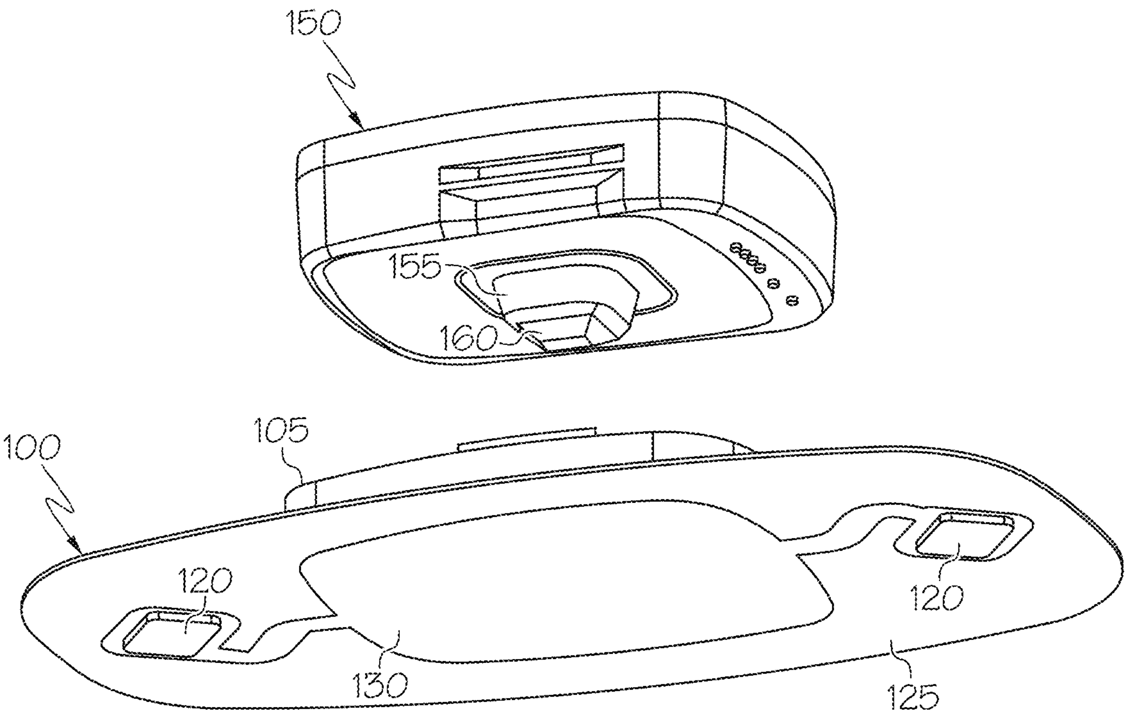
FIG. 1B illustrates a second perspective view of the example patch device according to various embodiments of the present disclosure.

FIG. 1B illustrates a second perspective view of the example patch device according to various embodiments of the present disclosure. As shown in FIG. 1B, the patch 100 includes a first adhesive layer 125, a second adhesive layer 130, and two electrocardiogram (ECG) electrodes 120 on each side of the patch 100.

In the embodiment shown, the first adhesive layer 125 spans substantially the entire bottom area of the patch 110, except for areas that are cut out (or where the first adhesive layer 125 defines openings) for the ECG electrodes 120 and second adhesive layer 130. As will be understood from discussions herein, the patch 100 may include any suitable number of adhesive layers or suitable openings/cut outs for different components, sensors, or features.

The second adhesive layer 130 may be any suitable size. As discussed above in relation to FIG. 1A, the second adhesive layer 130 may be sized to cover the opening 110. In the embodiment shown in FIG. 1B, the second adhesive layer 130 may span a cut out/opening in the first adhesive layer, which may generally be the size of the cradle 105 (or be any suitable size).

Figure 5:
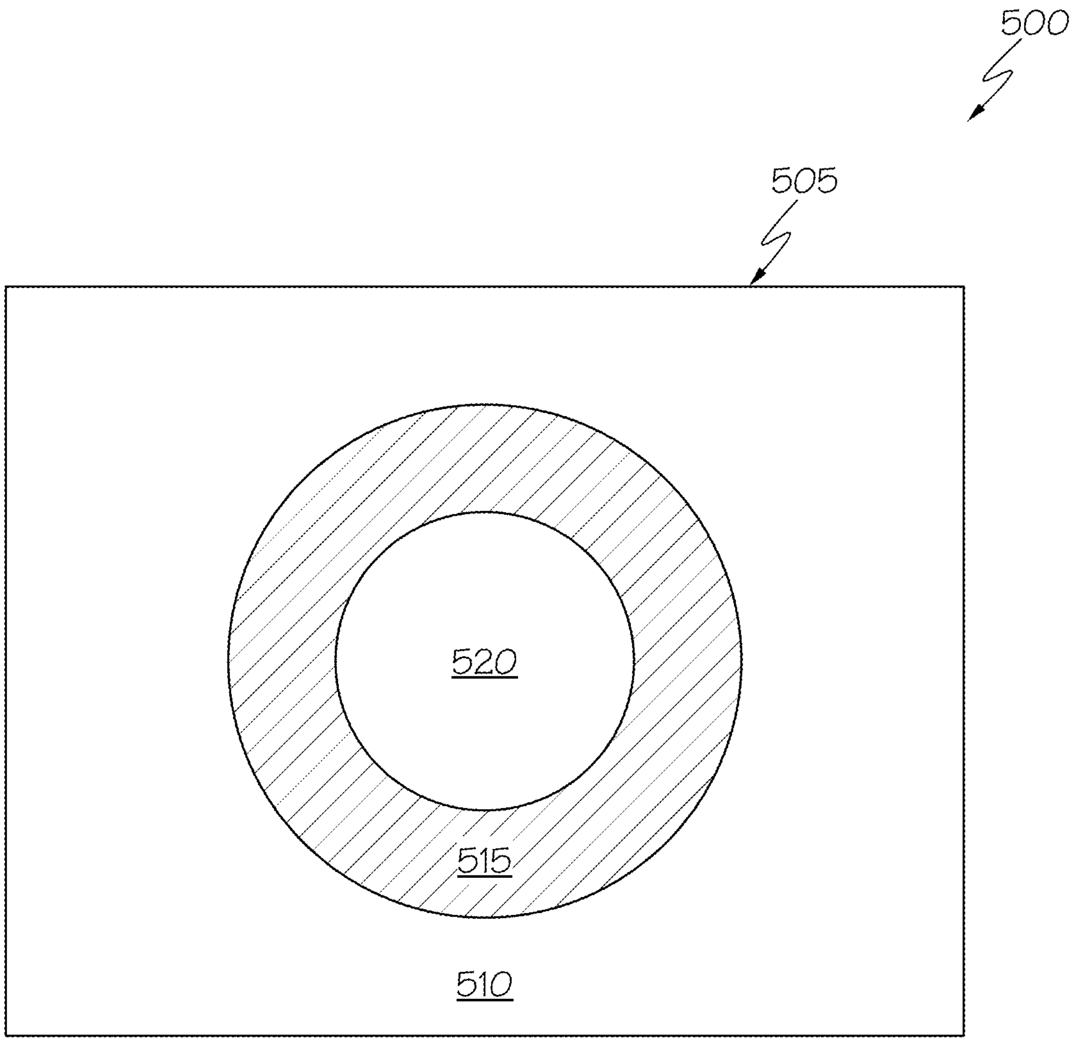
FIG. 5 illustrates various strain zones according to various embodiments of the present disclosure.

In one embodiment, the second adhesive layer 130 includes a third adhesive area 520 of FIG. 5 (as discussed herein).

The first adhesive layer 125 and the second adhesive layer 130 may include adhesives of any strength. According to an embodiment, the first adhesive layer 125 is first strength. In at least one embodiment, the first adhesive layer 125 is an adhesive made of silicon. In some embodiments, the second adhesive layer 130 is a second strength. According to an embodiment, the second adhesive layer is made of acrylic. In some embodiments, the first adhesive layer 125 is made of a weaker adhesive than the second adhesive layer 135. The adhesive layers discussed herein may be of any strengths. In one such embodiment, the first adhesive layer 125 and the second adhesive layer 130 are of the same or similar strengths. In further embodiments, the patch 100 includes fewer or more adhesive layers than discussed herein.

As shown in FIG. 1B, the pod 150 may include an elastic spacer 155 and a PPG sensor 160 (each of which are discussed further herein) extending from the pod 150. In some embodiments, the elastic spacer 155 and the PPG sensor 160 are integrally formed with the pod 150. In at least one embodiment, the elastic spacer 155 and the PPG sensor 160 are separate from the pod 150, but are operatively connected to the same during assembly of the pod 150. In one embodiment, the elastic spacer 155 and the PPG sensor 160 are connected to or attached to the cradle 105 or patch 100 (opposed to the pod 150).

The pod 150 may include additional computing components not shown. In at least one embodiment, the pod 150 connects to the PPG sensor via a PPG flexible printed circuit board (as further discussed herein). In some embodiments, the pod 150 includes additional computing components to receive, transmit, interpret, filter, and/or analyze information received from the PPG sensor 160 (and/or ECG electrodes 120). In one embodiment, the pod 150 includes a cellular, Bluetooth, or BLE antenna (or combination of antennas) for transmitting data received from the PPG sensor 160 to a computing system for analysis and/or diagnosis.

According to particular embodiments, the elastic spacer 155 and PPG sensor 160 extend a particular distance from the bottom of the pod 150. In at least one embodiment, the elastic spacer and the PPG sensor 160 extend approximately 0.1-10.0 mm from the bottom of the cradle 105. In some embodiments the elastic spacer 155 and the PPG sensor 160 extend less than 6.1 mm from the bottom of the pod 150.

Figure 1C:
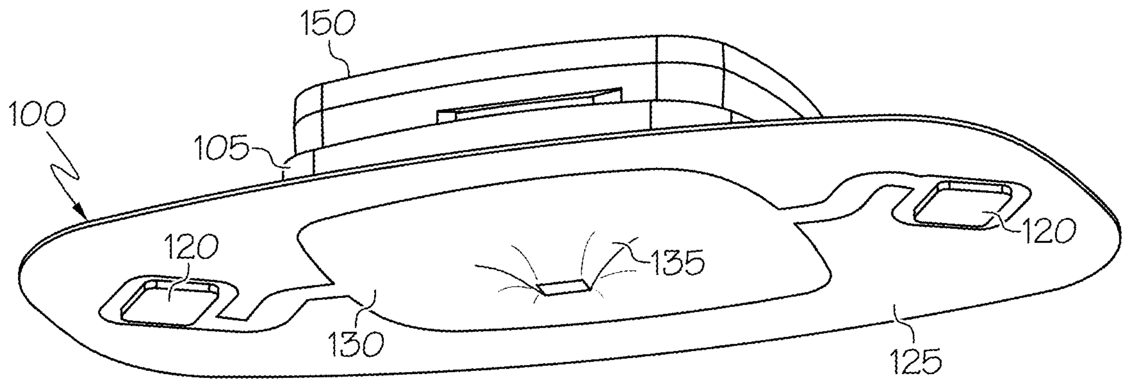
FIG. 1C illustrates a third perspective view of the example patch device according to various embodiments of the present disclosure.

FIG. 1C illustrates a third perspective view of the example patch device according to various embodiments of the present disclosure. In this embodiment, the pod 150 is attached to the patch 100 via the cradle 105. When the pod 150 is attached to the patch 100, the PPG sensor 160 may push on the second adhesive layer 130, creating a protrusion 135 (e.g., the elastic spacer 155 and the PPG sensor 160 extend through the opening 115 in the cradle 105, press on a non-adhesive side of the second adhesive layer 130, and deform the second adhesive layer 130). As will be further discussed in relation to FIG. 5, the various bottom features of the assembled pod 150 and patch 100 form various areas or zones. In a particular embodiment, the area of the protrusion 135 may have certain effects on the PPG signal quality. In these embodiments (and others), the second adhesive 130 that is not part of the protrusion 135, but is backed by the stiff cradle 105 and/or pod 150 forms a second area/zone (of strain isolation). In further embodiments, the area of the first adhesive 125 may form an additional/third area/zone.

Figure 2:
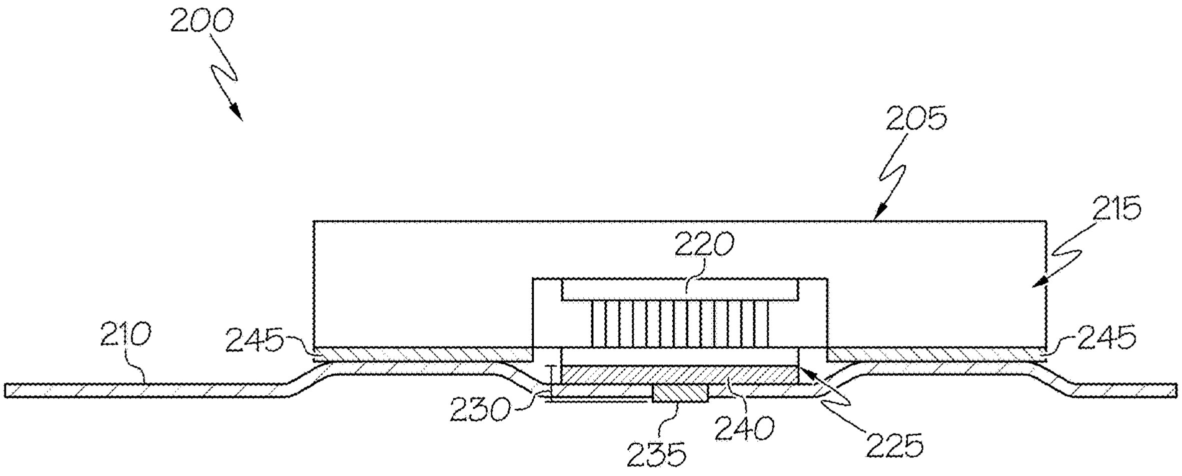
FIG. 2 illustrates a first perspective view of a PPG sensor cradle according to various embodiments of the present disclosure.

FIG. 2 illustrates a first perspective view of a PPG sensor cradle according to various embodiments of the present disclosure. As will be understood from discussions herein, the PPG sensor cradle 205 illustrates various components shown in a particular form to illustrate various effects of this arrangement, but the components shown may appear differently in other embodiments (e.g., as shown in FIGS. 1A-1C).

According to various embodiments and as illustrated in FIG. 2, the PPG sensor cradle 205 sits on top of a subject's skin 210 and is attached to the same via an adhesive layer 245 (which may correspond to second adhesive layer 130 shown in FIGS. 1A-1C).

The PPG sensor cradle 205 includes an enclosure 215. In one embodiment, the enclosure 215 houses various PPG sensor components. According to various embodiments, the enclosure 215 is rigid and may be made of various materials, including any suitable plastic or like rigid and lightweight material. The rigid enclosure may provide for additional pressure to be applied to a subject, as opposed to a flexible enclosure.

Additionally, the enclosure 215 may be any shape, including a trapezoidal shape as shown in FIG. 1.

According to one embodiment, the enclosure 215 includes a PPG sensor 235, a spacer 240, and an elastic spacer 225.

As shown in FIG. 2, the PPG sensor 235 extends beyond the adhesive layer 245 and presses into the subject's skin 210 via the spacer 240 and elastic spacer 220. In the embodiment shown in FIGS. 1A-1C, the second adhesive layer 130 (e.g., adhesive layer 245 in FIG. 2), extends over a protruding PPG sensor 160. It will be understood that in various embodiments, the adhesive 245 may extend over the PPG sensor 235 as shown in FIG. 2 and include the same general effects and features as discussed herein.

In one embodiment, the elastic spacer 220 sits within the enclosure 215. As shown in the embodiment in FIGS. 1A-1C, the elastic spacer 220 may extend from a bottom of an enclosure 215 (e.g., pod 150 and/or cradle 105).

In one or more embodiments, when the enclosure 215 is attached to the subject's skin 210 (via the adhesive 245), the adhesive and the elastic spacer 220 (and the spacer 240) apply a load to the PPG sensor 235 in the direction of the subject's skin 210. The elastic spacer 220 may be made of various elastic materials, including, for example, 2A silicone, rubber, or other flexible materials. According to various embodiments, the elastic spacer 220 includes a porous architecture. For example, the spacer 220 may include 2A silicone arranged into a lattice structure including a plurality of voids.

As will be understood from discussions herein, the elastic spacer 220 may enable the PPG sensor 235 to be in conformal contact with the subject's skin 210 (e.g., the PPG sensor 235 can tilt/move with the subject's skin 210 via deformation/compression of the elastic spacer 220). In some embodiment, this allows a PPG sensor 235 (discussed further below) to continue reading data from a subject, even when the subject rolls or breathes.

According to one embodiment, the PPG sensor cradle includes a gap 230 measuring from the first adhesive layer 245 and the bottom of the PPG sensor 235. According to one embodiment, this gap 230 may provide a backing force applied on the PPG sensor 235. This backing force may enhance signal quality of the readings from the PPG sensor 235. In various embodiments, the applied load biases the PPG sensor 235 toward the skin and ensures the PPG sensor 235 remains in conformity with the skin regardless of subject motion or other dislodging phenomena. As will be understood from discussions herein, the gap 230 may be created by any arrangement and number of components (e.g., spacers, portions of a cradle, portions of a patch, etc.). In at least one embodiment, the gap 230 may be about 0.1 mm, 0.2 mm, 0.1-2.0 mm, 1.1 mm or less, 0.1-10 mm, 6.1 mm or less, or any suitable distance.

According to one embodiment, a combination of features of the PPG cradle 205 may isolates a region from strain (e.g., create a strain isolation area). In at least one embodiment, isolation from strain causes the region of skin to remain taut (e.g., unfolded, unwrinkled, etc.) regardless of the subject's motion and despite any warps or other changes to skin surrounding the region of strain isolation. As shown in FIG. 2, the gap 230 and force applied by the various components shown therein at least partially causes skin 210 directly under a portion of the PPG cradle 205 surround the elastic spacer 220 to pull the subject's skin 210 upwards toward the PPG cradle 205, creating an area of strain isolation.

In one or more embodiments, the combination of the strain isolation and continuous conformity between the PPG sensor 235 and the skin provides for more accurate and precise PPG sensor readings.

Figure 3:
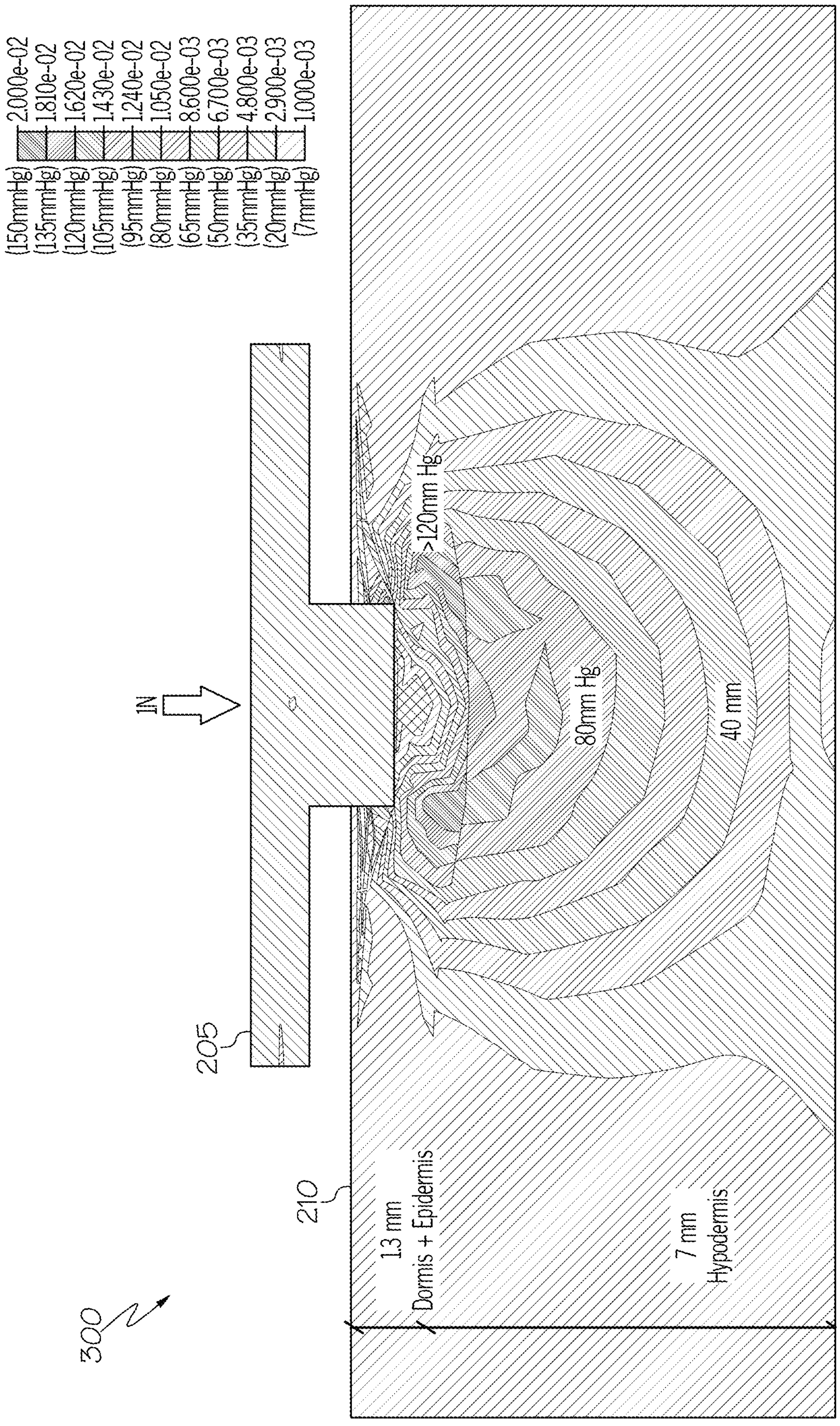
FIG. 3 illustrates pressure effects of an exemplary PPG sensor/device on a patient's skin according to various embodiments of the present disclosure.

FIG. 3 shows pressure effects on a patient's skin from an exemplary PPG sensor/device, according to various embodiments of the present disclosure.

According to at least one embodiment, the PPG sensor cradle 205 may be in contact with a subject's skin 210. In various embodiments, an amount of force applied relates to the gap 230 as discussed with reference to FIG. 2. The force may be created due to the gap 230 and the adhesives applied to a subject's skin. Additionally, in one embodiment, the subject's body mass index (BMI) impacts the amount of force applied.

Figure 8A:
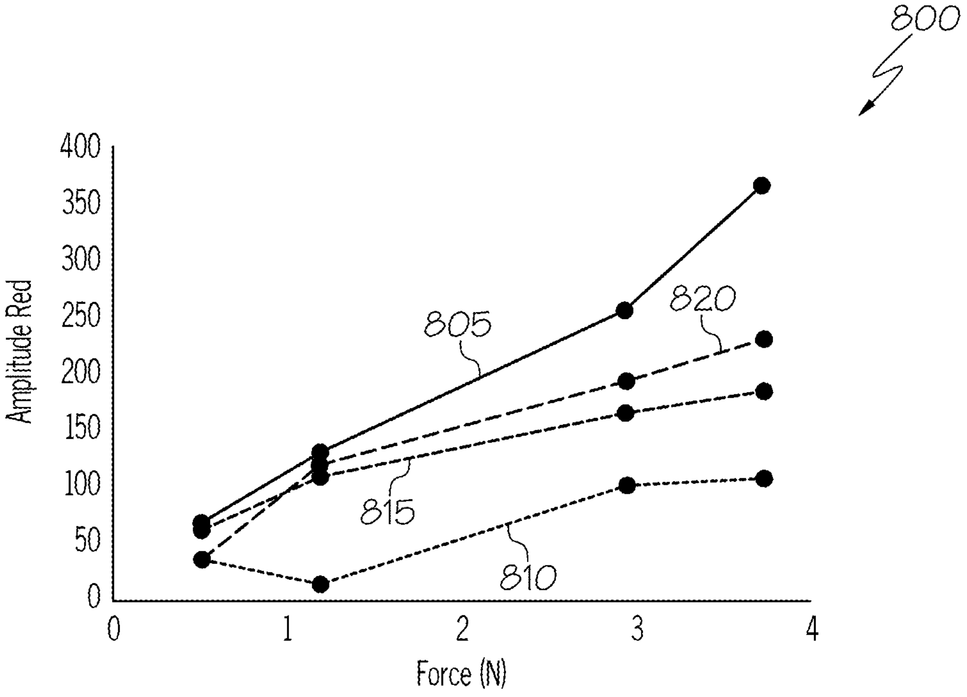
FIG. 8A illustrates a fifth set of data points according to various embodiments of the present disclosure.
Figure 8B:
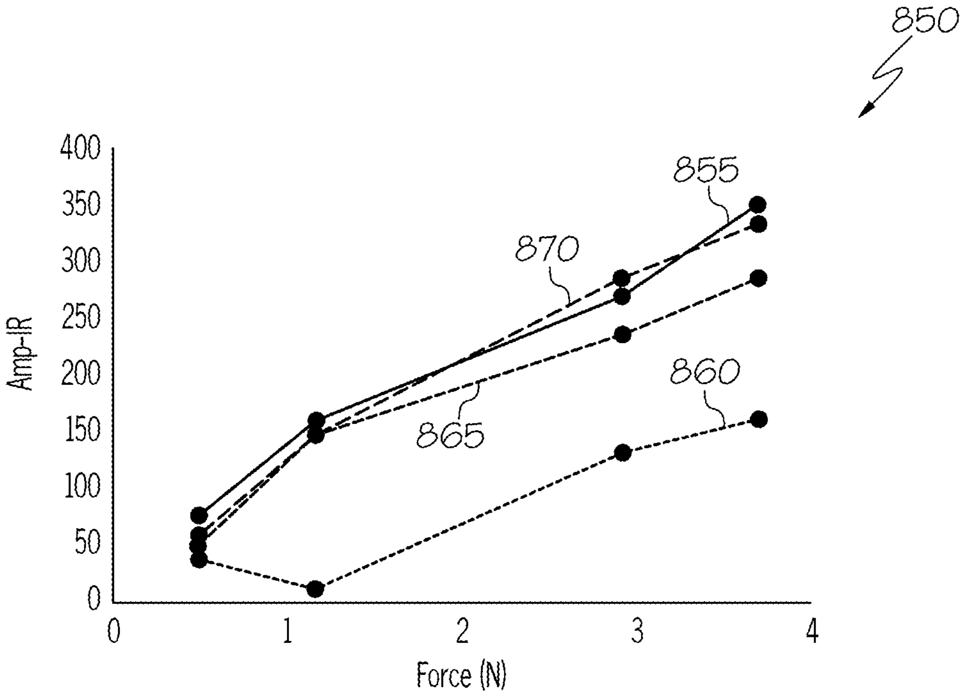
FIG. 8B illustrates a sixth set of data points according to various embodiments of the present disclosure.

For example, and as illustrated in FIG. 3, one (1) Newton (N) of force is applied to the PPG sensor cradle 205. This 1N of force may be created from the gap between the first adhesive layer 245 and the bottom of the PPG sensor 235, as discussed with reference to FIG. 2. As illustrated, the force may differ depending on the size of the gap 230 and the subject's BMI. As shown, the patient's skin and underlying tissue experiences varying levels of pressure (expressed in mmHg). As shown in FIGS. 8A and 8B, increasing force/load may increase PPG signal amplitude.

As will be understood, maintaining force and skin conformality with the PPG sensor and patient's skin may lead to higher levels of repeatability. Further, in one or more embodiments, the gap 230 and force applied by the various components shown herein applies a pressure to the tissue under skin 210 directly under a portion of the PPG cradle 205 as shown in FIG. 3 that matches or exceeds diastolic pressure (e.g., about 80 to 120 mmHg) to minimize the effect of venous or deoxygenated blood content that provides more accurate and precise PPG sensor readings.

Figure 4A:
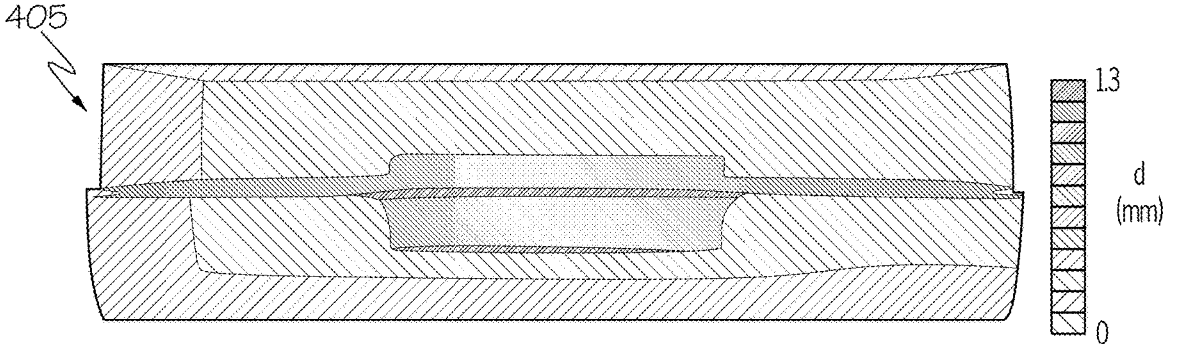
FIG. 4A illustrates a depth of a PPG sensor on a patient's skin according to various embodiments of the present disclosure.
Figure 4B:
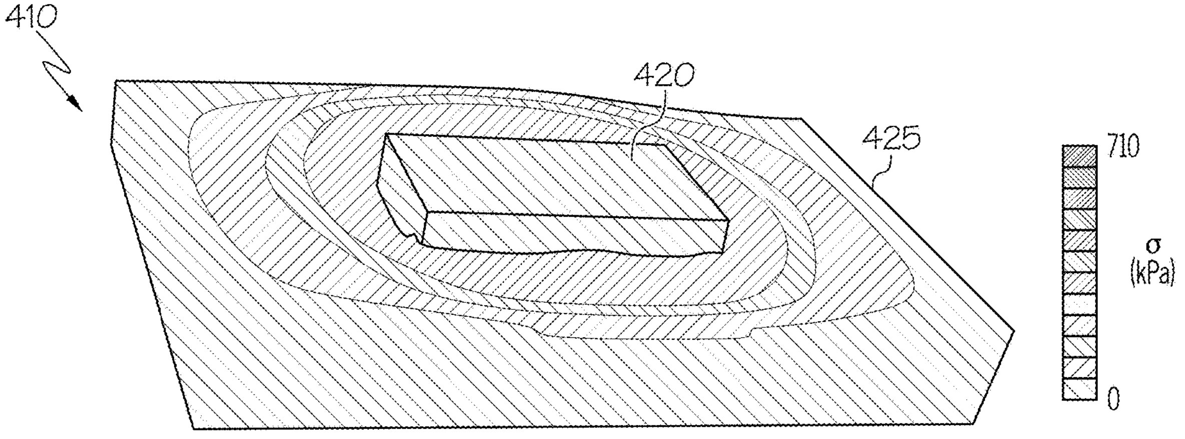
FIG. 4B illustrates a pressure exerted by a PPG sensor on a patient's skin according to various embodiments of the present disclosure.
Figure 4C:
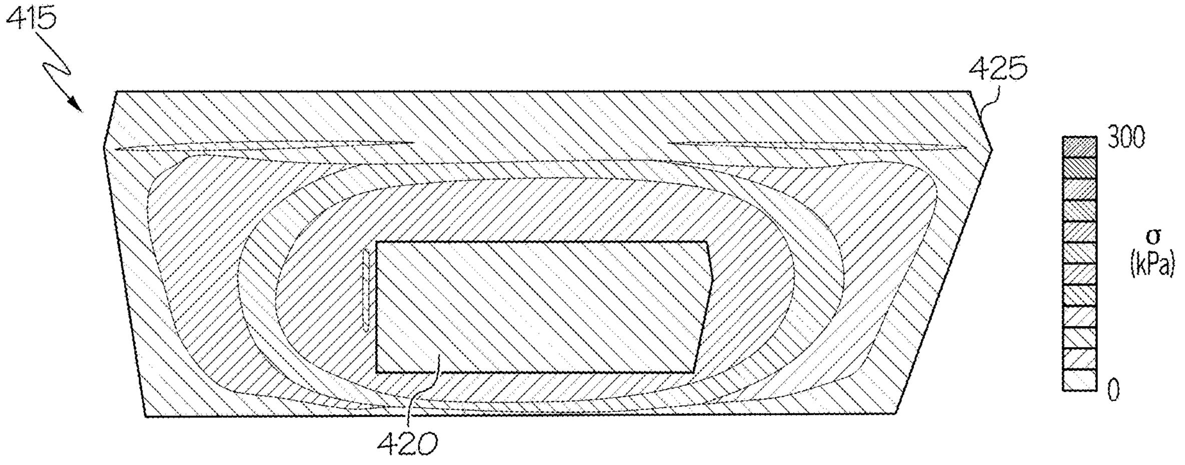
FIG. 4C illustrates a pressure exerted by a PPG sensor on a patient's skin according to various embodiments of the present disclosure.

FIG. 4A illustrates a view of the PPG sensor cradle according to various embodiments of the present disclosure. FIG. 4A demonstrates maintaining a constant depth (shown in mm) that can be achieved using the systems and methods here (e.g., spacers, gaps, rigid enclosures). FIG. 4B illustrates a view of the PPG sensor cradle according to various embodiments of the present disclosure. FIG. 4B shows that a relatively consistent pressure (in kPa) is achieved through the techniques and devices discussed herein even when a patient's skin tilts or rocks (e.g., when a patient moves). FIG. 4C illustrates a view of the PPG sensor cradle according to various embodiments of the present disclosure. FIG. 4C shows that consistent pressure (in kPa) is maintained by the techniques and devices herein when a patient rolls (e.g., during a sleep test).

According to one embodiment, the PPG sensor cradle 205 may sit at different angles. As illustrated by a first view 405 of the PPG sensor cradle 205, the PPG sensor cradle 205 may sit flat. As shown in FIGS. 4B and 4C, even as a patient rotates, in various embodiments, the system/device shown herein maintains a relatively consistent pressure on the patient's skin, thus resulting in relatively consistent PPG readings/signals.

As illustrated by a second view 410 and third view 415, the PPG sensor cradle 205 may sit at an angle. For example, if the PPG sensor cradle 205 is attached to a subject, the subject may breathe or roll and adjust the angle of chest while keeping the PPG sensor cradle attached and capable of adjusting in accordance with such breathing.

Moreover, depending on the amount of force applied to the PPG sensor cradle 205, the PPG sensor cradle 205 may be prevented from rocking. As discussed with reference to FIG. 3, when 1N of force is applied, the PPG sensor cradle 205 is pressed onto a subject's skin. Thus, the increased pressure leads to decreased rocking (if any) of the PPG sensor cradle 205. The increased pressure of the underlying tissue can also match or exceed diastolic pressure to remove venous or deoxygenated blood content from data derived from the PPG sensor to provide more accurate and precise PPG sensor readings.

FIG. 5 illustrates various strain zones according to particular embodiments of the present disclosure. FIG. 5 shows zones on a patient's skin and the effects of different corresponding areas of various embodiments of devices/systems discussed here.

In one embodiment, FIG. 5 includes an affected area 505, which may correspond to the example patch device 105 in accordance with FIG. 1. According to various embodiments, the affected area 505 may include a first adhesive area 510, a second adhesive area 515, and a third adhesive area 520. In one embodiment, the first adhesive area 510 may correspond to the first adhesive layer 125 of FIGS. 1A-1C (FIG. 2 does not include an area corresponding to first adhesive layer 125 of FIGS. 1A-1C). According to one embodiment, the second adhesive area 515 may correspond to the second adhesive layer 130 of FIG. 1 and adhesive layer 245 of FIG. 2. The second adhesive area 515 may be a stronger adhesive than the first adhesive area 510. In one embodiment, the third adhesive area 520 may be made of the same adhesive as the second adhesive area 515. According to one embodiment, the third adhesive area 520 may correspond to the second adhesive layer 245 plus the PPG sensor 235 of FIG. 2 or the second adhesive layer 130 and the protrusion 135 of FIGS. 1A-1C.

In one embodiment, the weaker first adhesive area 510 prevents a subject from irritation or bruising where the adhesive attaches to the subject's skin. However, because the first adhesive area 510 is weaker, the subject's skin may move.

According to various embodiments, the stronger second adhesive area 515 is backed by the enclosure 215 of FIG. 2 or the cradle 105 (and/or pod 150) of FIG. 1. In at least one embodiment, the rigid backing leads to increased strength of attachment of the adhesive and the subject's skin and helps prevent irritation or bruising, despite a stronger adhesive. According to particular embodiments, the second adhesive area 515 is an area of strain isolation as discussed herein.

In various embodiments, the stronger third adhesive area 520 sits below the PPG sensor 235 of FIG. 2. However, the PPG sensor 235 is not directly attached to the third adhesive area 520. Rather, the PPG sensor 235 sits behind (from the perspective of a patient's skin) the third adhesive area 520; this allows for the PPG sensor 235 to move freely behind the third adhesive area 520, leading to conformality of the sensor and increased accuracy of data collected form the subject. In one embodiment, force is applied to the third adhesive area 520, as discussed above with reference to FIG. 3.

Figure 6A:
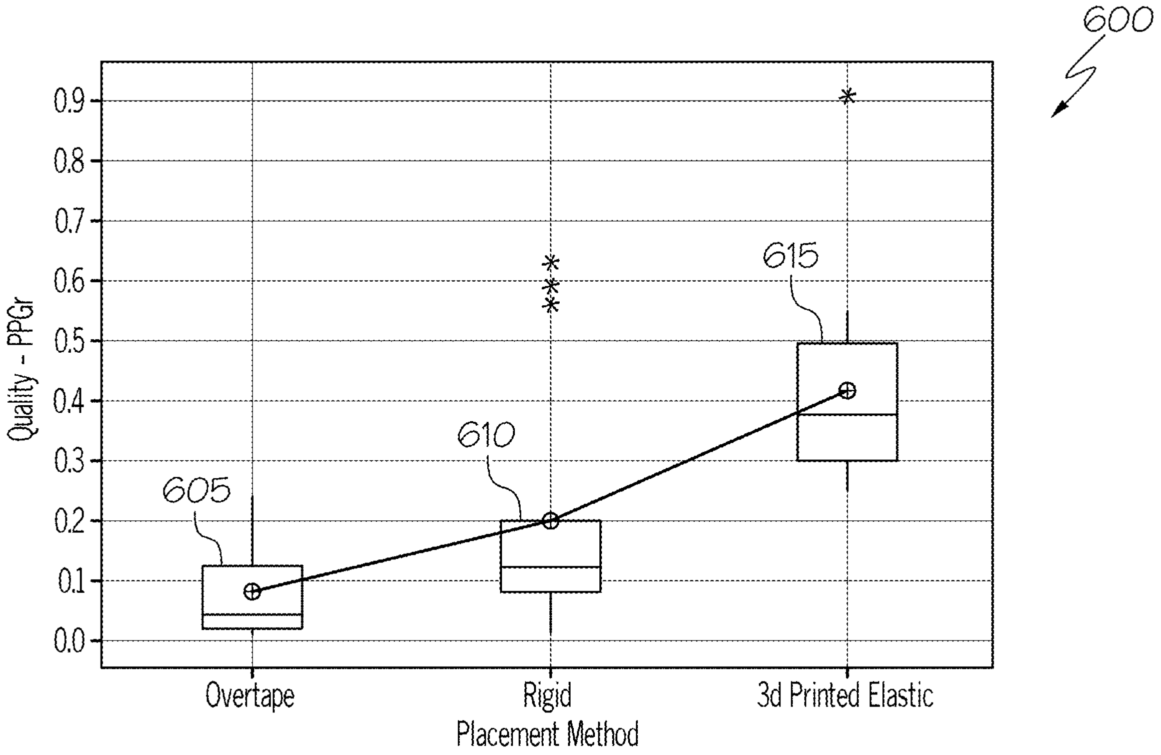
FIG. 6A illustrates a first set of data points according to various embodiments of the present disclosure.
Figure 6B:
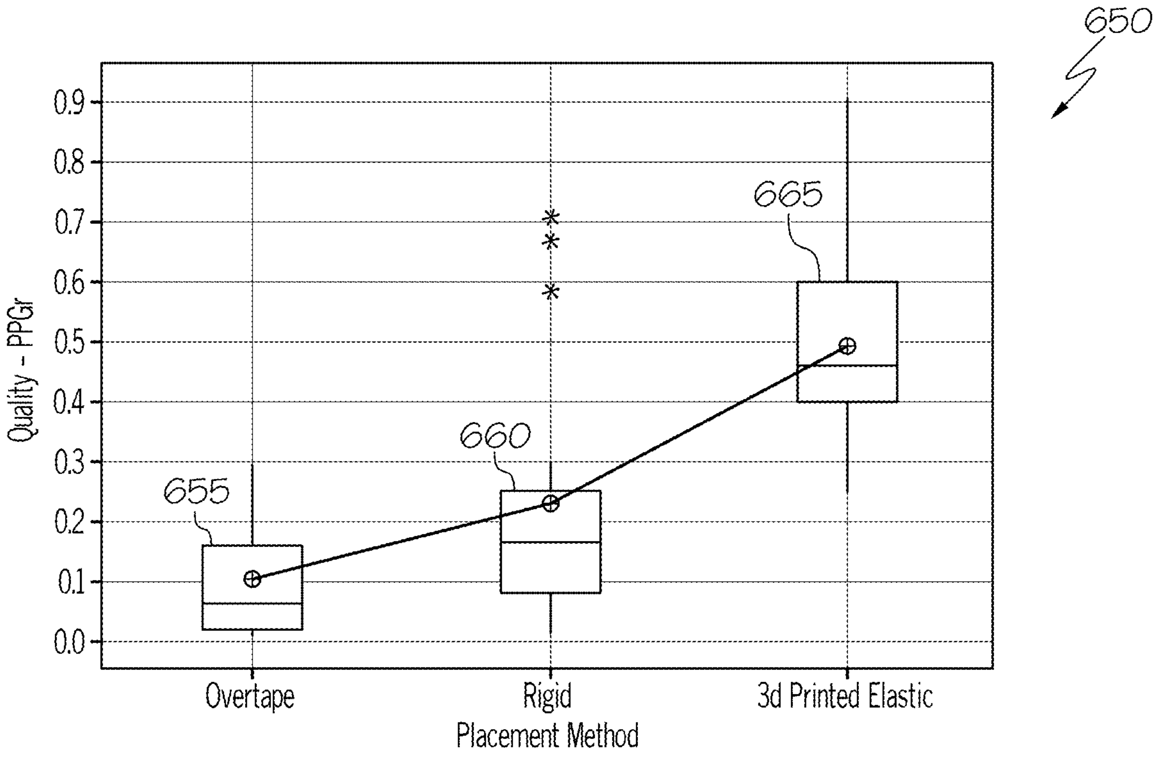
FIG. 6B illustrates a second set of data points according to various embodiments of the present disclosure.

FIG. 6A illustrates a first set of data points according to various embodiments of the present disclosure. FIG. 6B illustrates a second set of data points according to various embodiments of the present disclosure. According to various embodiments, graphs 600 and 650 illustrate the correlation between the PPG attachment mechanism and the quality of various PPG data points collected from a subject. FIGS. 6A and 6B show a quality of signal for PPG red (PPGr) and infrared (PPGi) signals based on three different attachment mechanisms: 1) overtape (e.g., PPG sensor is taped to patient's chest); 2) rigid placement method (e.g., PPG sensor is attached to patient's chest via a rigid structure (e.g., a PPG cradle or like structure discussed herein); and 3) 3D printed elastic (e.g., the combination of a rigid structure and an elastic spacer as discussed herein).

Graph 600 illustrates the impact of placement method on the quality of PPGr. At block 605, overtape is used for placement of the PPG sensor. The use of overtape has a lower quality of PPGr than the other two placement mechanisms. As shown in FIG. 6A, PPGr signal quality using overtape is about 0.025 to 0.125.

At block 610, a rigid placement of the PPG sensor is used. The rigid placement leads to increased quality of the PPGr relative to the use of overtape. As shown in FIG. 6A, PPGr signal quality using a rigid placement method is about 0.075 to 0.200.

At block 615, 3D printed elastic is used (e.g., in combination with a rigid structure). In the embodiment shown, the use of an elastic spacer in combination with a rigid structure greatly increases the quality of PPGr relative to both the overtape and rigid placement because the PPG sensor is conformally attached to the patient (e.g., as discussed herein, the PPG sensor can tilt/rock/move via compression of the elastic spacer to maintain strong contact with a patient's skin). As shown in FIG. 6A, use of the 3D printed elastic mechanism results in a PPGr quality of about 0.300 to 0.500.

Graph 650 illustrates the impact of placement method on the quality of PPGi. At block 655, overtape is used for placement of the PPG sensor. The use of overtape has a lower quality of PPGi than the other two placement mechanisms. As shown in FIG. 6B, PPGi quality when using an overtape mechanism is about 0.025 to 0.160.

At block 660, a rigid placement of the PPG sensor is used. The rigid placement leads to increased quality of the PPGi relative to the use of overtape. As shown in FIG. 6B, PPGi quality when using a rigid placement mechanism is about 0.085 to 0.250.

At block 665, 3D printed elastic is used in the placement of the PPG sensor (in combination with a rigid structure). The use of an elastic spacer greatly increases the quality of PPGi relative to both the overtape and rigid placement. As shown in FIG. 6B, PPGi quality when using 3D printed elastic is about 0.400 to 0.610.

Figure 7A:
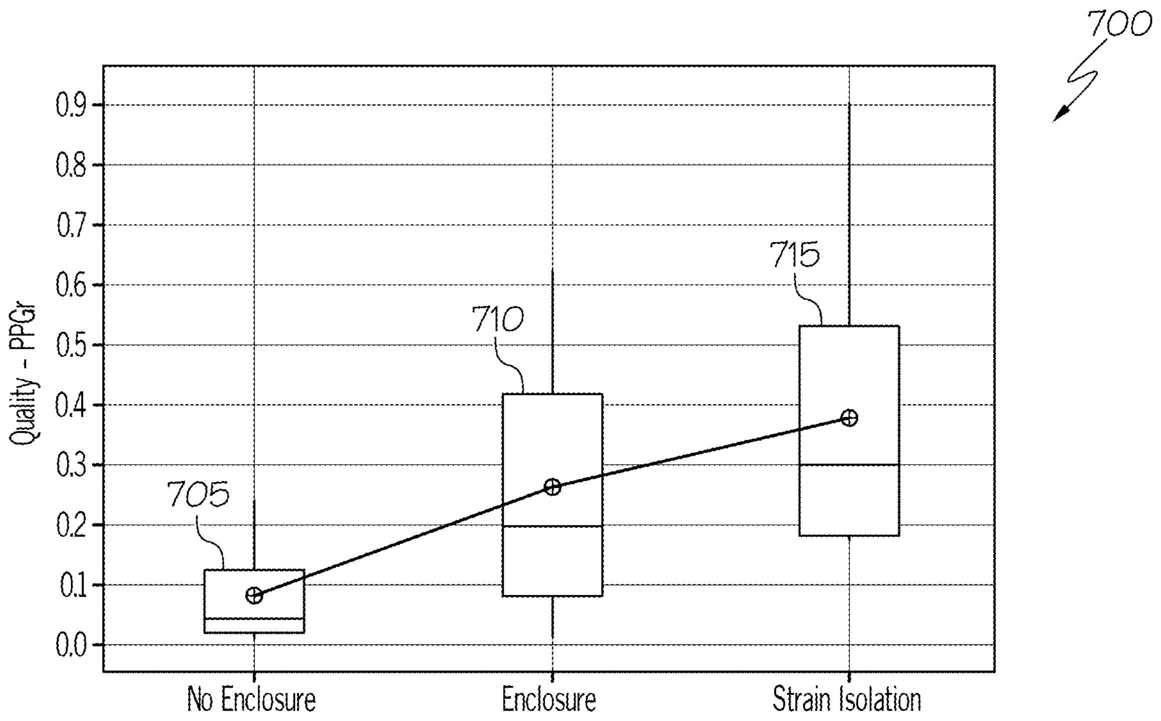
FIG. 7A illustrates a third set of data points according to various embodiments of the present disclosure.
Figure 7B:
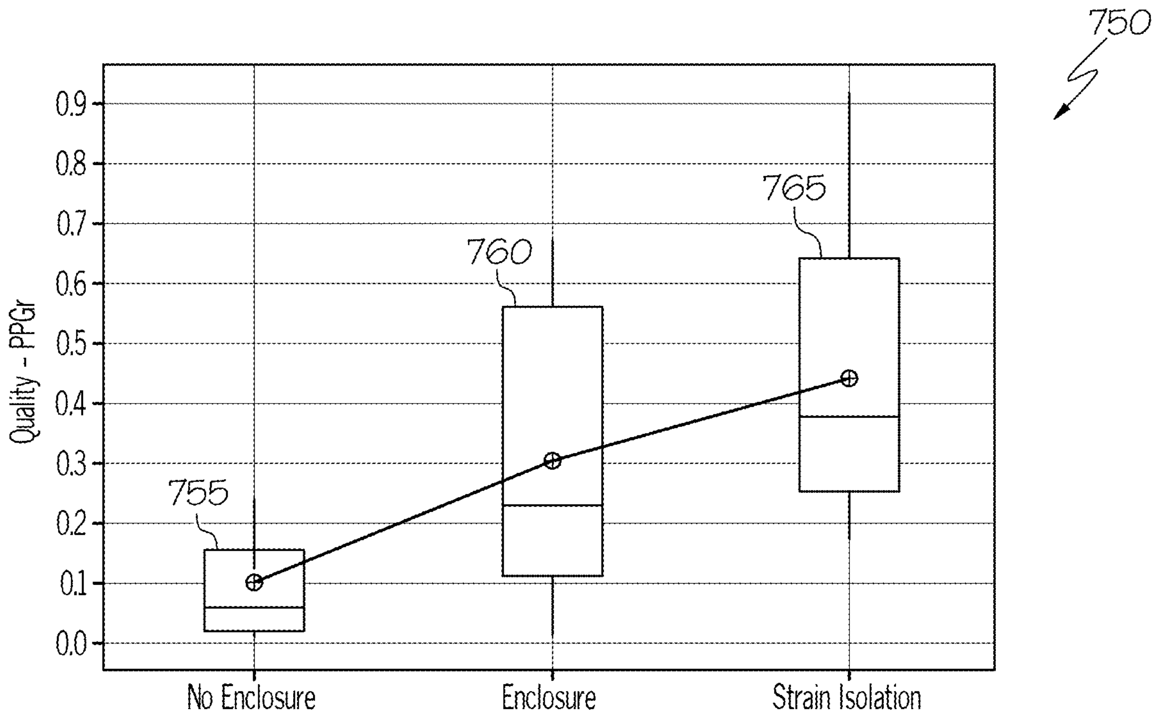
FIG. 7B illustrates a fourth set of data points according to various embodiments of the present disclosure.

FIG. 7A illustrates a third set of data points according to various embodiments of the present disclosure. FIG. 7B illustrates a fourth set of data points according to various embodiments of the present disclosure.

According to various embodiments, graphs 700 and 750 illustrate a correlation between the enclosure method of a PPG sensor and the quality of various PPG data points collected from a subject. As shown in graphs 700 and 750, a number of enclosure environments were tested: 1) no enclosure (e.g., PPG sensor just taped or otherwise attached to a patient); 2) a rigid enclosure (e.g., a relatively small footprint "enclosure" or rigid backing); and 3) a strain isolating rigid enclosure (e.g., an enclosure with a larger footprint that surrounds the PPG sensor and any spacers, effectively strain isolating the PPG sensor and creating the various zones shown in FIG. 5).

Graph 700 illustrates the impact of the enclosure method on the quality of PPGr. At block 705, no enclosure is used. The use of no enclosure leads to a lower quality of PPGr than other enclosure mechanisms. As shown in FIG. 7A, no enclosure results in a PPGr of about 0.025 to 0.125.

At block 710, an enclosure is used. The use of the enclosure leads to increased quality of the PPGr relative to the use of no enclosure. As shown in FIG. 7B, a rigid (but not a strain isolating enclosure) results in a PPGr of about 0.085 to 0.425.

At block 715, strain isolation is used. The use of strain isolation greatly increases the quality of PPGr relative to both the use of no enclosure or the use of an enclosure. As shown in FIG. 7A, use of a strain isolating enclosure (such as those discussed herein, including as shown in FIGS. 1 and 2) results in a PPGr of about 0.185 to 0.525).

Graph 750 illustrates the impact of the enclosure method on PPGi. At block 755, no enclosure is used. The use of no enclosure leads to a lower quality of PPGi compared to other enclosure mechanisms. As shown in FIG. 7B, no enclosure results in PPGi of about 0.025 to 0.160.

At block 760, an enclosure is used (e.g., but not a strain isolating enclosure). The use of the enclosure leads to increased quality of the PPGi relative to the use of no enclosure. As shown in FIG. 7B, a non-strain isolating enclosure results in a PPGi of about 0.115 to 0.560.

At block 765, strain isolation is used. The use of strain isolation greatly increases the quality of PPGi relative to both the use of no enclosure or the use of an enclosure. As shown in FIG. 7B, a strain isolating enclosure results in a PPGi of about 0.250 to 0.630.

FIG. 8A illustrates a fifth set of data points according to various embodiments of the present disclosure. FIG. 8B illustrates a sixth set of data points according to various embodiments of the present disclosure.

According to various embodiments, the graphs 800 and 850 illustrate the correlation between the force applied to the PPG sensor and amplitude of red and infrared (IR) signals collected from a subject. Each of lines 805, 855, 810, 860, 815, 865, 820, and 870, correspond to different subjects or different tests. According to one embodiment, the various points on the line correspond to 0.5N, 1.2N, 3N, and 3.75N applied to the subject's skin via the PPG sensor cradle.

In one embodiment, the force applied may correspond to FIG. 3. As shown, when more force is applied to the PPG sensor (e.g., against the subject's skin), the amplitude red and amplitude IR increases in strength. Thus, as illustrated, the force may increase the amplitude of signals received from a PPG sensor.

Figure 9:
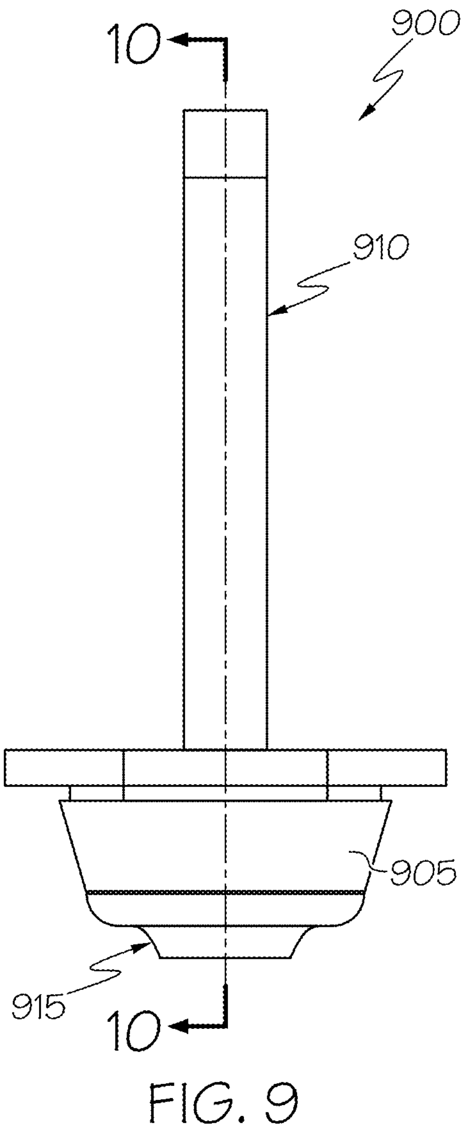
FIG. 9 illustrates a first perspective view of a PPG sensor assembly according to various embodiments of the present disclosure.

FIG. 9 illustrates a first perspective view of a PPG sensor assembly according to various embodiments of the present disclosure. The PPG sensor shown in FIGS. 9-14 may correspond to the PPG sensor shown in FIGS. 1A-1C (e.g., shown as part of the pod 150).

In one embodiment, the PPG sensor may include a first silicone layer 905, a PPG flexible printed circuit board (PCB) 910, and a second silicone layer 915. In one embodiment, the silicone layer 905 corresponds to the spacer 155 of FIGS. 1A-1C. In another embodiment, 905 and 915 are a single silicone layer. FIG. 9 includes a cross-sectional line 10-10 indicating the cross-section shown in FIG. 10

Figure 10:
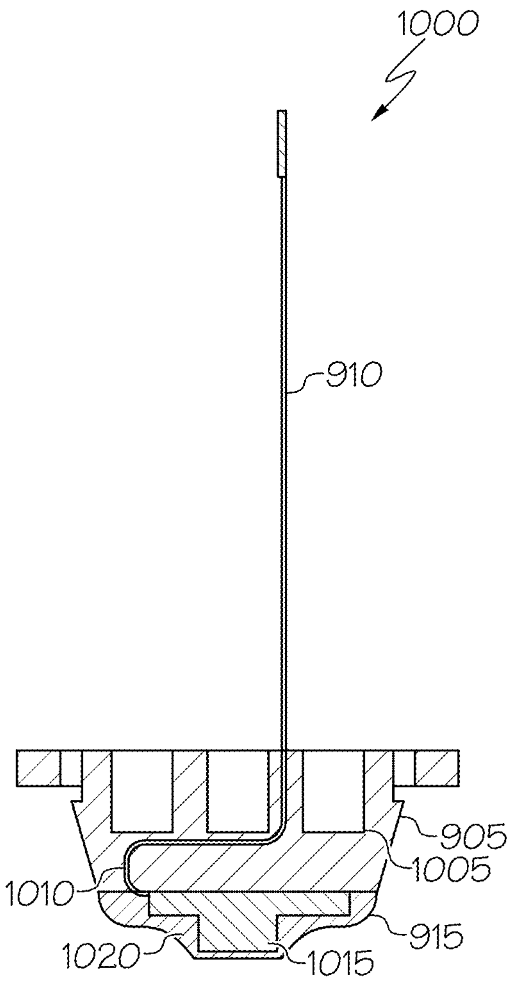
FIG. 10 illustrates a cross-sectional view of the PPG sensor according to various embodiments of the present disclosure.

FIG. 10 illustrates a cross-sectional view of the PPG sensor according to various embodiments of the present disclosure. As shown, the PPG sensor may be viewed along the 10-10 cross section. This view of the PPG sensor shows exemplary internal components of the first silicone layer 905, a PPG printed circuit board 910, and a second silicone layer 915, as discussed with reference to FIG. 9. In the embodiment shown, the first silicone layer 905 is an elastic spacer with one or more pores or otherwise voided structure 1005. Further, in various embodiments, the PPG sensor includes PPG sensing components (e.g., red and IR components) shown at 1015, which may be encased in plastic or another protective barrier as shown (e.g., 1020). As also shown in the embodiment of FIG. 10, a portion of the PPG printed circuit board 1010 weaves or otherwise passes through the spacer/first silicone layer 905 to connect the PPG sensor to corresponding computing components included in a pod (e.g., pod 150).

As will be understood from discussions herein, in various embodiments, the spacer/first silicone layer 905 may compress or otherwise deform such that the PPG sensor is in conformal contact with a patient's skin. In these embodiments (and others), the PPG printed circuit board 910 is flexible at least to withstand the compression of the spacer/first silicone layer 905. In one embodiment, particular portions of the PPG printed circuit board 910 are flexible (e.g., portion 1010). In further embodiments, the entire PPG printed circuit board 910 is flexible.

Figure 11:
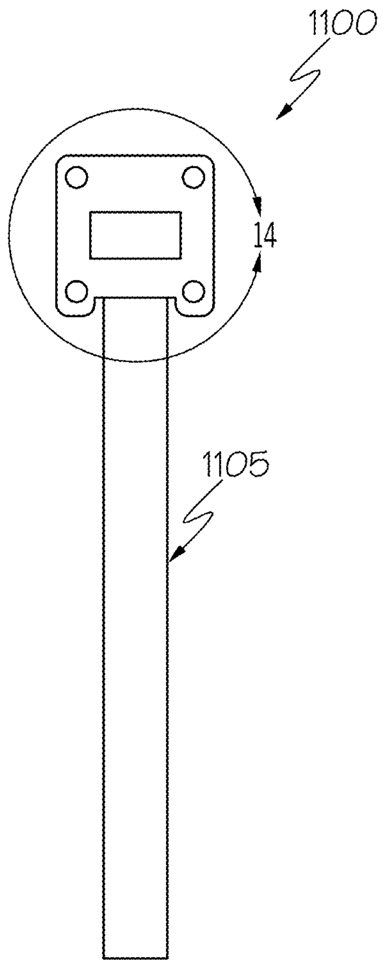
FIG. 11 illustrates a perspective view of a portion of the PPG sensor assembly according to various embodiments of the present disclosure.

FIG. 11 illustrates a perspective view of a portion of the PPG sensor assembly according to various embodiments of the present disclosure. According to various embodiments, the PPG sensor may include a PPG printed circuit board 1105, which in one embodiment, may correspond to the PPG printed circuit board 910 of FIG. 9.

Figure 12:
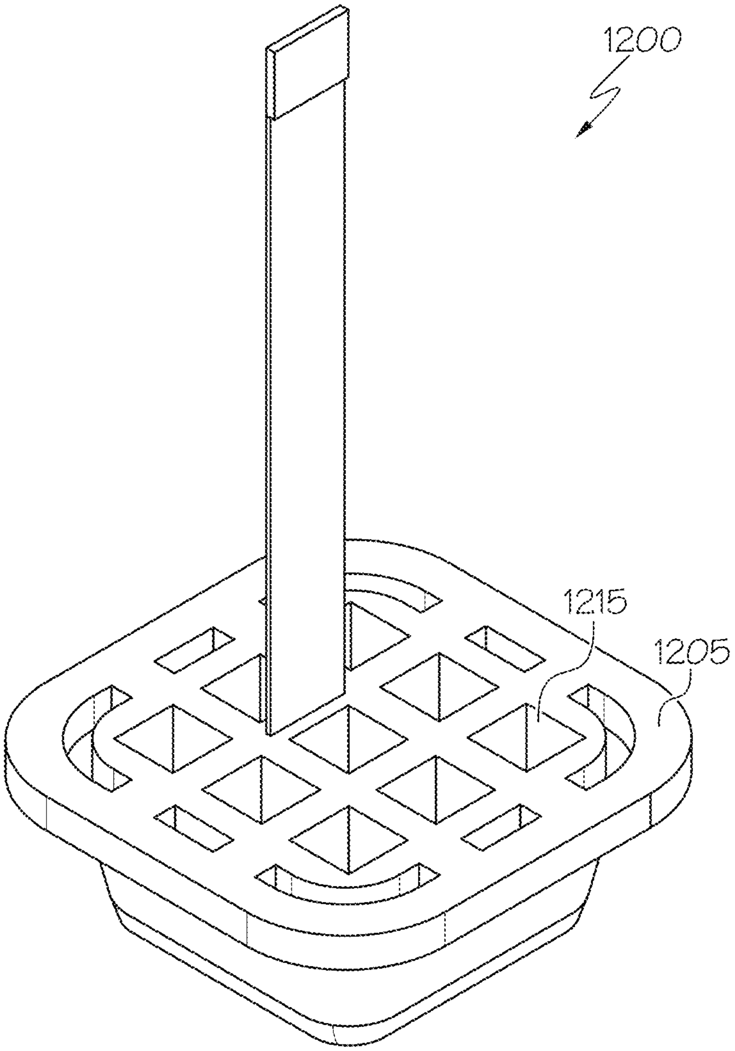
FIG. 12 illustrates a perspective view of the PPG sensor assembly according to various embodiments of the present disclosure.

FIG. 12 illustrates a perspective view of the PPG sensor assembly according to various embodiments of the present disclosure. In the embodiment shown, the PPG sensor includes a support structure 1205 connected to the first silicone layer (e.g., elastic spacer) 905. In at least one embodiment, the support structure includes various holes/voids (or pores) 1210 that may result in weight reduction.

The support structure 1205 may be constructed of any suitable material. In at least one embodiment, the support structure is constructed of a hard plastic material and is used for operatively connecting the PPG sensor with a pod casing (or other suitable structure).

Figure 13:
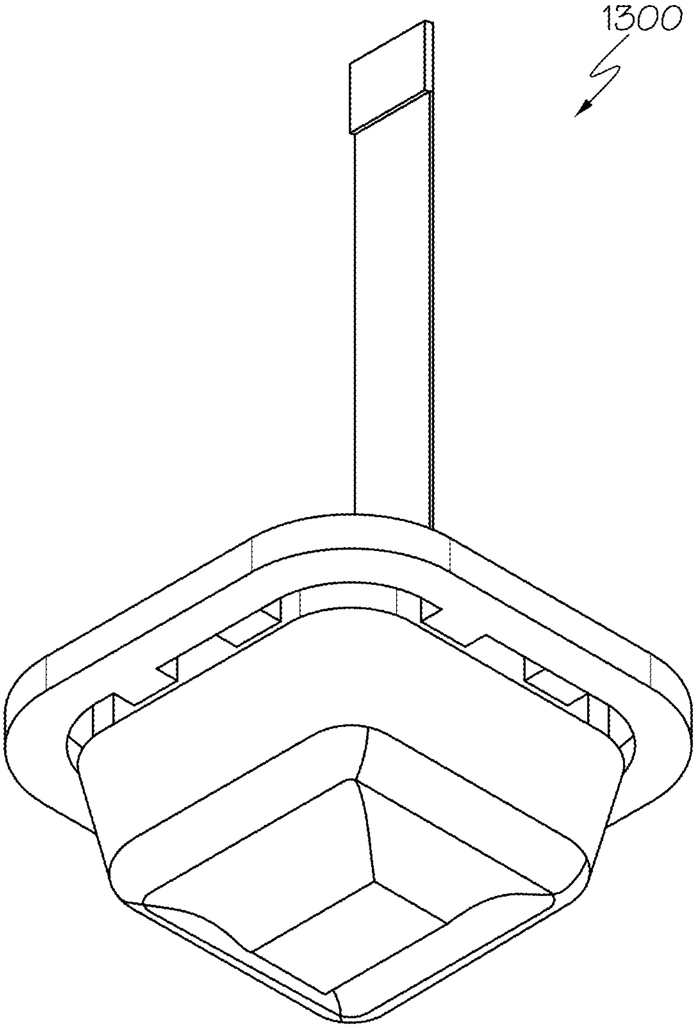
FIG. 13 illustrates a perspective view of the PPG sensor assembly according to various embodiments of the present disclosure.

FIG. 13 illustrates a perspective view of the PPG sensor assembly according to various embodiments of the present disclosure.

Figure 14:
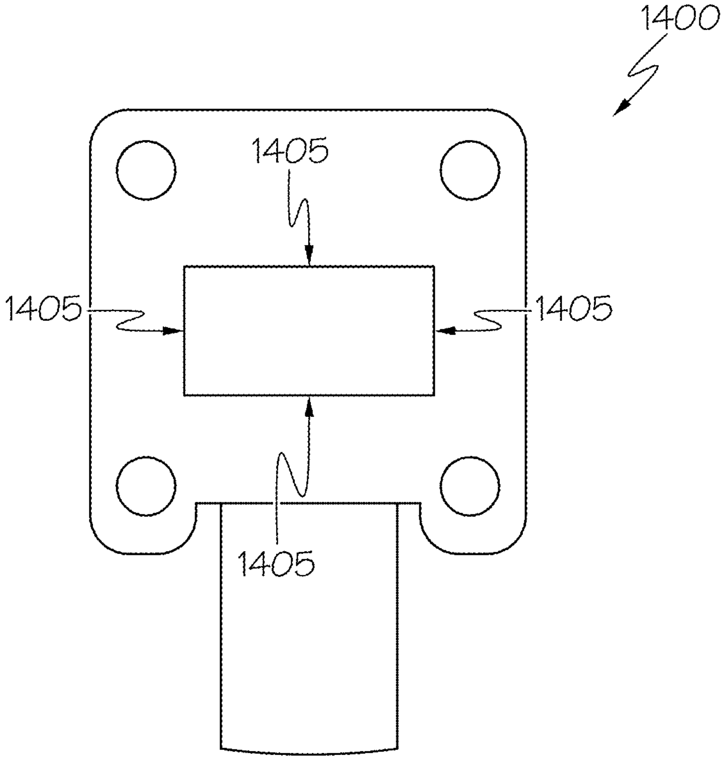
FIG. 14 illustrates a perspective view of a portion of the PPG sensor assembly according to various embodiments of the present disclosure.

FIG. 14 illustrates a perspective view of a portion of the PPG sensor assembly according to various embodiments of the present disclosure. According to one embodiment, this perspective view shows the top of the PPG sensor assembly and the top of the PPG printed circuit board 910 of FIG. 9. In various embodiments, the PPG printed circuit board 910 may include a gap-filling adhesive 1405.

The foregoing description of the exemplary embodiments has been presented only for the purposes of illustration and description and is not intended to be exhaustive or to limit the inventions to the precise forms disclosed. Many modifications and variations are possible in light of the above teaching.

One such variation includes a device/patch that includes a force sensor associated with a PPG sensor to measure the amount of force exerted on a patient via the patch. In these embodiments (and others), the force may be tunable via an elastic spacer backing the PPG sensor and/or a vertical distance between the PPG sensor and a bottom of a rigid structure (e.g., cradle).

In further embodiments, a patch includes force sensors and multiple PPG sensors. In these embodiments (and others), a rigid support structure includes openings for, or is otherwise operatively connected to, multiple PPG sensors with elastic or other backings (such as those PPG sensors with elastic spacers discussed herein). Continuing with this embodiment, each PPG sensor of the multiple PPG sensors exerts a different force (resulting in a different pressure) on a patient's skin. As will be understood, in the embodiments above, a system may receive data from the force sensors and multiple PPG sensors and be able to calculate or otherwise determine a patient's blood pressure.

In still further embodiments, a patch includes one or more PPG sensors (which may or may not be associated with or connected to an elastic spacer) associated with one or more force sensors, where the force exerted on a patient's skin may be tunable via an actuator, motor, or other mechanical mechanism for adjusting a vertical distance between the one or more PPG sensors and a portion of a rigid support structure. In alternate embodiments, the patch includes a spacer connected to at least one of the one or more PPG sensors, where the spacer degrades, is a shape memory polymer, or otherwise changes over time to decrease (or increase) a vertical distance, compressibility of the spacer (so the spacer compresses more or less), or otherwise changes the force on a patient's skin over time.

The embodiments were chosen and described in order to explain the principles of the inventions and their practical application so as to enable others skilled in the art to utilize the inventions and various embodiments and with various modifications as are suited to the particular use contemplated. Alternative embodiments will become apparent to those skilled in the art to which the present inventions pertain without departing from their spirit and scope. Accordingly, the scope of the present inventions is defined by the appended claims rather than the foregoing description and the exemplary embodiments described therein.

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable nonvolatile memories such as secure digital (SD), flash memory, memory stick, etc., or any other medium which can be used to carry or store computer program code in the form of computer-executable instructions or data structures and which can be accessed by a computer.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a computer to perform one specific function or a group of functions.

Those skilled in the art will understand the features and aspects of a suitable computing environment in which aspects of the disclosure may be implemented. Although not required, some of the embodiments of the claimed inventions may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represents examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multiprocessor systems, microprocessor-based or programmable consumer electronics, networked PCs, minicomputers, mainframe computers, and the like. Embodiments of the claimed invention are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the inventions are embodied. The logical connections between computers include a local area network (LAN), a wide area network (WAN), virtual networks (WAN or LAN), and wireless LAN s (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the invention is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed inventions will be readily discernible from the description herein, by those of ordinary skill in the art. Many embodiments and adaptations of the disclosure and claimed inventions other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed inventions. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed inventions. In addition, some steps may be carried out simultaneously, contemporaneously, or in synchronization with other steps.

The embodiments were chosen and described in order to explain the principles of the claimed inventions and their practical application so as to enable others skilled in the art to utilize the inventions and various embodiments and with various modifications as are suited to the particular use contemplated. Alternative embodiments will become apparent to those skilled in the art to which the claimed inventions pertain without departing from their spirit and scope. Accordingly, the scope of the claimed inventions is defined by the appended claims rather than the foregoing description and the exemplary embodiments described therein.

Any logic or application described herein may be implemented and structured in a variety of ways. For example, one or more applications described may be implemented as modules or components of a single application. Further, one or more applications described herein may be executed in shared or separate computing systems or a combination thereof. For example, more than one application may execute in the same computing system, or in multiple computing systems in the same computing environment. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The invention claimed is:

1. A patch comprising:
- an adhesive layer defining an adhesive layer opening;
- a rigid support structure comprising a bottom surface area defining a rigid support structure opening for a photoplethysmography (PPG) sensor and an enclosure for housing a compressible spacer; and
- the PPG sensor extending through the rigid support structure opening and the adhesive layer opening, thereby configured for directly contacting skin of a patient, wherein the PPG sensor comprises:
  - a first side and a second side, wherein:
    - the first side of the PPG sensor is within the rigid support structure; and
    - the second side of the PPG sensor is a vertical distance from the bottom surface area of the rigid support structure and is configured for directly contacting the patient's skin; and
  - the compressible spacer operatively connected to the first side of the PPG sensor, wherein the patch is configured to be attached to the patient's skin, such that when the patch is attached to the patient's skin the adhesive layer is configured to attach to a portion of the patient's skin corresponding to at least a portion of the bottom surface area of the rigid support structure.

2. The patch of claim 1, wherein, when the patch is attached to the patient's skin, the second side of the PPG sensor is configured to press into the patient's skin.

3. The patch of claim 2, wherein when the PPG sensor is pressed into the patient's skin, the patch is configured to exert an amount of pressure on the patient which is at least partially based on the vertical distance.

4. The patch of claim 3, wherein when the patch is attached to the patient's skin, the adhesive layer and the bottom surface of the rigid support structure strain isolate the PPG sensor.

5. The patch of claim 3, wherein the vertical distance is 10 mm or less.

6. The patch of claim 1, wherein the compressible spacer is elastic.

7. The patch of claim 6, wherein the compressible spacer is silicone.

8. The patch of claim 7, wherein the compressible spacer is porous.

9. The patch of claim 1, further comprising a flexible printed circuit board (PCB) connected to first side of PPG sensor.

10. The patch of claim 9, wherein the PCB collects signal data from the PPG sensor.

11. The patch of claim 10, wherein the data from the PPG sensor is transmitted to a computing system.

12. The patch of claim 1, wherein:
- the adhesive layer is a first adhesive layer; and
- the patch further comprises a second adhesive layer.

13. The patch of claim 12, wherein the first adhesive is made of a first material and the second adhesive layer is made of a second material.

14. The patch of claim 13, wherein the first material is the same as the second material.

* * * * *